US012023396B2

(12) United States Patent
Schmaus et al.

(10) Patent No.: US 12,023,396 B2
(45) Date of Patent: Jul. 2, 2024

(54) FLAVOUR AND FRAGRANCE COMPOSITIONS COMPRISING ACETOPHENONE DERIVATIVES

(71) Applicant: Symrise AG, Holzminden (DE)

(72) Inventors: Gerhard Schmaus, Höxter (DE); Sabine Lange, Holzminden (DE); Manuel Pesaro, Beverungen (DE)

(73) Assignee: Symrise AG, Holzminden (DE)

( * ) Notice: Subject to any disclaimer, the term of this patent is extended or adjusted under 35 U.S.C. 154(b) by 187 days.

(21) Appl. No.: 14/753,761

(22) Filed: Jun. 29, 2015

(65) Prior Publication Data

US 2015/0374599 A1 Dec. 31, 2015

(30) Foreign Application Priority Data

Jun. 30, 2014 (EP) .................... 14174916

(51) Int. Cl.

| | | |
|---|---|---|
| *A61K 8/35* | (2006.01) | |
| *A61Q 5/02* | (2006.01) | |
| *A61Q 11/00* | (2006.01) | |
| *A61Q 13/00* | (2006.01) | |
| *A61Q 15/00* | (2006.01) | |
| *C11B 9/00* | (2006.01) | |
| *C11D 3/00* | (2006.01) | |
| *C11D 3/20* | (2006.01) | |
| *C11D 3/50* | (2006.01) | |
| *C11D 7/26* | (2006.01) | |
| *A61L 9/01* | (2006.01) | |

(52) U.S. Cl.
CPC ............. *A61K 8/35* (2013.01); *A61Q 5/02* (2013.01); *A61Q 11/00* (2013.01); *A61Q 13/00* (2013.01); *A61Q 15/00* (2013.01); *C11B 9/0061* (2013.01); *C11D 3/0068* (2013.01); *C11D 3/2072* (2013.01); *C11D 3/50* (2013.01); *C11D 7/264* (2013.01); *A61K 2800/262* (2013.01); *A61K 2800/49* (2013.01); *A61L 9/01* (2013.01)

(58) Field of Classification Search
None
See application file for complete search history.

(56) References Cited

U.S. PATENT DOCUMENTS

| | | | | | |
|---|---|---|---|---|---|
| 3,528,097 | A * | 9/1970 | Ogo | ............. | G03G 9/135 430/115 |
| 5,120,709 | A * | 6/1992 | Cella | ............. | A61K 8/046 512/2 |
| 6,379,682 | B1 * | 4/2002 | Tchinnis | ............. | A61K 8/06 524/588 |
| 7,282,524 | B2 * | 10/2007 | Gray | ............. | B01F 17/0042 510/123 |
| 8,263,814 | B2 * | 9/2012 | Waibel | ............. | B01D 11/0488 568/913 |
| 8,309,111 | B2 * | 11/2012 | Fernandez de Castro | ............. | A61P 31/02 424/405 |
| 2006/0002880 | A1 * | 1/2006 | Peffly | ............. | A61K 8/44 424/70.13 |
| 2006/0110415 | A1 | 5/2006 | Gupta | | |
| 2009/0016976 | A1 * | 1/2009 | Turin | ............. | C07C 31/13 424/65 |
| 2009/0224206 | A1 | 9/2009 | Braun et al. | | |
| 2013/0059924 | A1 | 3/2013 | Scheurich et al. | | |
| 2016/0000670 | A1 | 1/2016 | Pesaro et al. | | |

FOREIGN PATENT DOCUMENTS

| | | | |
|---|---|---|---|
| EP | 0574086 A2 | * | 12/1993 |
| EP | 2181690 A1 | * | 5/2010 |
| WO | 98/56340 A1 | | 12/1998 |
| WO | WO-2004075900 A2 | * | 9/2004 |
| WO | WO-2008061187 A1 | * | 5/2008 |
| WO | WO-2012147042 A2 | * | 11/2012 |
| WO | 2014/135650 A1 | | 9/2014 |
| WO | 2014/135666 A1 | | 9/2014 |
| WO | WO-2014135650 A1 | * | 9/2014 |

OTHER PUBLICATIONS

STN Registry No. 99-93-4. "4'-Hydroxyacetophenone". STN Registry File. Retrieved Jun. 23, 2016. One Page.*
Senatore F. "Composition of the Essential Oil of Chuquiraga spinosa (R. et P.) D. Don". Flavour Fragrance Journal. 1996; 11:215-217.*
Krammer et al. "Glyosidically Bound Aroma Compounds in the Fruits of Prunus Species: Apricot (P. armeniaca, L.), Peach (P. persica, L.), Yellow Plum (P. domestica, L.ssp. Syriaca)". J. Agric. Food Chem. 1991; 39:778-781.*
Health Matter Program (2011). "Water Amounts in Fruits and Vegetables". Retrieved from the Internet: Jun. 24, 2016. <http://www.rrtcadd.org/resources/Advocacy/Water-Amounts-in-Fruits-and-Vegetables---Handout-Week-10.pdf>. One Page.*
Greger et al. "Characterization of the Key Aroma Compounds in Apricots (Prunus armeniaca) by Application of the Molecular Sensory Science Concept". Journal of Agricultural and Food Chemistry. 2007; 55:5221-5228.*
USDA National Nutrient Database for Standard Reference. "Apricots, Raw". Retrieved from the Internet: Dec. 21, 2016. <https://ndb.nal.usda.gov/ndb/foods/show/2140>. pp. 1-6.*
Lotzkar et al. "Pectin as an Emulsifying Agent: Comparative Effciencies of Pectin, Tragacanth, Karaya, and Acacia". Industrial and Engineering Chemistry. 1943; 35(12):1294-1297.*
Baker RA. "Reassessment of Some Fruit and Vegetable Pectin Levels". Journal of Food Science. 62(2); 1997:225-229.*
Katona et al. "Simultaneous Determination of Sugars, Sugar Alcohols, Acids and Amino Acids in Apricots by Gas Chromatography-Mass Spectrometry". Journal of Chromatography A. 1999; 847:91-102. (Year: 1999).*

(Continued)

*Primary Examiner* — Leslie A. Royds Draper
(74) *Attorney, Agent, or Firm* — Dilworth & Barrese, LLP

(57) ABSTRACT

Suggested are new flavour and fragrance compositions comprising selected acetophenone derivatives for dissolving flavours and fragrances, and further especially for dissolving lipophilic compounds, which are implemented in these products.

2 Claims, No Drawings

(56) References Cited

OTHER PUBLICATIONS

USDA AMD Agricultural Analytics Division, USDA National Organic Program. "Glycerin" (Technical Evaluation Report). Published Jun. 10, 2013. pp. 1-19. (Year: 2013).*

Cassiday L. "Emulsions: Making Oil and Water Mix". Inform Magazine (American Oil Chemists' Society). Apr. 2014. pp. 1-11. (Year: 2014).*

\* cited by examiner

FLAVOUR AND FRAGRANCE COMPOSITIONS COMPRISING ACETOPHENONE DERIVATIVES

FIELD OF INVENTION

The present invention belongs to the area of cosmetic and household products and refers to flavour and fragrance compositions comprising selected acetophenone derivatives for dissolving flavours and fragrances, and further especially for dissolving lipophilic compounds, which are implemented in these products.

STATE OF THE ART

Cosmetic and household products are often perfumed to meet the requirements of the consumers. The important functions of fragrances are to provide pleasant odors, to mask the base smell of the product, and also to give the product an odoring identity.

However, since fragrances are usually poorly water-soluble or insoluble compounds it is often difficult to perfuming the products. The use of emulsifiers and surfactants is nowadays a standard solubilization technique to improve the solubility of fragrances (and also for lipophilic substances) in preparations. But their use as solubilizing agents often leads to further different problems, such as causing cloudiness and turbidity in transparent formulations, skin irritation, and sensitization to light. Furthermore, another big problem in the use of fragrances in products is their high loss rate and the rapid decreases during storage due to volatilization, evaporation, oxidation and poor stability.

A further substance class, which shows the same solubility problems in (cosmetic and household) products like fragrances and flavours, are lipohphilic compounds. A large number of lipophilic molecules have very low solubilities in (cosmetic) solvents and have a tendency to recrystallize or separate rapidly. It is known in the art to combine certain compounds, like e.g. DHEA (Dehydroepiandrosteron), in order to solve the solubility problems of lipophilic compounds. Further, it is known practice to encapsulate lipophilic compounds in micelles of block copolymers, for example poly(ethylene oxide-propylene oxide) diblock or triblock copolymers to solubilizing the lipophilic compounds. However, these block copolymers do not satisfactorily dissolve the lipophilic compound.

Thus, there is still a big demand for compounds and substances which show the ability to improve the solubility of fragrances and flavours, especially lipophilic flavours and fragrances, and other lipophilic compounds in general, and thus improving the stability of the preparation, e.g. against flocculation, coalescence or creaming.

Therefore, the object of the present invention was to identify a multi-functional additive for cosmetic, pharmaceutical and household formulations, which is able to improve the solubility of fragrances and flavors, and especially lipophilic compounds. It is important that the identified additive should not negatively interact with other ingredients of the formulations. The invention further objects to identify an additive which, in particular, have the mentioned properties in regard to flavours and fragrances and at the same time show additional improving characters concerning the stability and solubility of lipophilic components in general, e.g. plant oils, neutral oils and fatty acid esters, especially in water-based formulations. Both features lead to a stabilized system in which, especially flavours and fragrances are stabilized thus to improve and/or enhance the long lasting impression of flavours and fragrances on the one hand. On the other hand the identified additive should show a good fat dissolving ability, thus lipohilic components e.g. like lipophilic flavours and fragrances can be more easily dissolved and, thus contribute to avoidance of phase separation and instability of the formulations.

DESCRIPTION OF THE INVENTION

Object of the present invention is the use of a composition comprising at least one acetophenone derivative of formula (I):

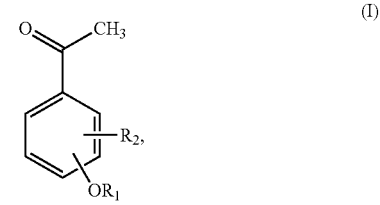

in which
$R_1$ denotes hydrogen or methyl, and
$R_2$ denotes hydrogen, hydroxyl or a —OCH3 group,
or a cosmetically or pharmaceutically acceptable salt thereof,
  (i) to improve the stability and/or solubility of flavours and fragrances and/or
  (ii) to improve the stability and/or solubility of lipophilic components and/or
  (iii) to improve and/or enhance the long lasting impression of flavours and fragrances in a cosmetic, pharmaceutical or household formulation or
  (iv) to inhibit and/or decrease and/or counteract malodour, such as body odour or maladour originated from kitchen, bathroom or smoke.

A further object is the use of a composition comprising at least one acetophenone derivative of formula (I):

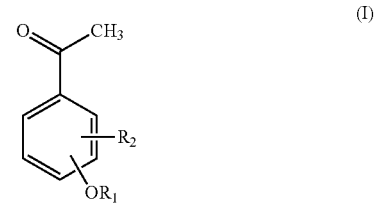

in which
$R_1$ denotes hydrogen or methyl, and
$R_2$ denotes hydrogen, hydroxyl or a —OCH3 group,
or a cosmetically or pharmaceutically acceptable salt thereof,
  as a lipophilic-component-solubilization system in cosmetic, pharmaceutical or household formulations.

Lipophilic-component-solubilization system in the sense of the present invention is a system which may comprises various ingredients and which is especially created with the focus to apply to preparations and formulations in order to improve and/or enhance the solubilisation of compounds, in particular lipohphilic compounds and/or fragrances and/or flavours.

The lipophilic components of the present invention maybe selected from lipids, fatty acid esters, polymers, plant oils, neutral oils or any molecule which have lipophilic character. The lipohilic components may also be a lipophilic flavouring agent or fragrances (e.g. an essential oil) or any other lipophilic substance with a HLB value of lower than 20, preferably a HLB value lower than 15, more preferably lower than 10.

Lipophilic flavor and fragrances in the sense of the present invention may be selected from various chemical groups, such as for example: the group comprising hydrocarbons, such as for example 3-carene; a-pinene; beta-pinene; alpha-terpinene; p-cymol; bisabolene; camphene; caryophyllene; cedrene; farnesene; limonene; longifolene; myrcene; ocimene; valencene; (E,Z)-1,3,5-undecatrien; the group comprising aliphatic alcohols, such as for example: hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; the group comprising aliphatic aldehydes and the acetals thereof such as for example: hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethylacetal; 1,1-dimethoxy-2,2,5-trimethyl-4-hexene; the group comprising aliphatic ketones and oximes thereof, such as for example: 2-heptanone; 2-octanone; 3-octanone; 2-nonanone; 5-methyl-3-heptanone; 5-methyl-3-heptanone oxime; 2,4,4,7-tetramethyl-6-octen-3-one; aliphatic sulfur-containing compounds such as for example: 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol; the group comprising aliphatic nitriles, such as for example: 2-nonenoic acid nitrile; 2-tridecenoic acid nitrile; 2,12-tridecadienoic acid nitrile; 3,7-dimethyl-2,6-octadienoic acid nitrile; 3,7-dimethyl-6-octenoic acid nitrile; the group comprising aliphatic carboxylic acids esters such as for example: (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; the group comprising acyclic terpene alcohols such as for example: citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates, 3-methyl-2-butenoates thereof; the group comprising acyclic terpene aldehydes and ketones such as for example: geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal; the group comprising cyclic terpene alcohols such as for example: menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates thereof; the group comprising cyclic terpene aldehydes and ketones such as for example: menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4-a-methanonaphthalen-8(5H-)-one; nootkatone; dihydronootkatone; alpha-sinensal; beta-sinensal; the group comprising cyclic alcohols such as for example: 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol; the group comprising cycloaliphatic alcohols such as for example: alpha-3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol; the group comprising esters of cycloaliphatic carboxylic acids such as for example: allyl-3-cyclohexyl propionate; allylcyclohexyl oxyacetate; methyldihydrojasmonate; methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate; the group comprising aromatic hydrocarbons, such as for example styrene and diphenylmethane;

the group comprising araliphatic alcohols such as for example: benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenyl ethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol; the group comprising esters of araliphatic alcohols and aliphatic carboxylic acids such as for example: benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethylacetate; alphatrichloromethylbenzyl acetate; alpha,alpha-dimethylphenylethyl acetate; alpha, alpha-dimethylphenylethyl butyrate; cinnamyl acetate; 2-phenoxyethyl isobutyrate; 4-methoxybenzyl acetate; araliphatic ethers such as for example: 2-phenylethyl methyl ether; 2-phenyl ethyl isoamyl ether; 2-phenyl ethyl-1-ethoxyethyl ether; phenylacetaldehyde dimethylacetal; phenylacetaldehyde diethylacetal; hydratropaldehyde dimethylacetal; phenylacetaldehyde glycerol acetal; the group comprising aromatic and araliphatic aldehydes such as for example: benzaldehyde; phenylacetaldehyde; 3-phenylpropanal; hydratropaldehyde;

4-methylbenzaldehyde; 4-methylphenylacetaldehyde; 3-(4-ethylphenyl)2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal; the group comprising aromatic and araliphatic ketones such as for example: acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanol; benzophenone; the group comprising aromatic and araliphatic carboxylic acids and the esters thereof such as for example: benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenylglycidate; ethyl-3-methyl-3-phenyl glycidate; the group comprising nitrogenous aromatic compounds such as for example: 2,4,6-trinitro-1,3-dimethyl-5-tert.-butylbenzene; 3,5-dinitro-2,6-dimethyl-4-tert.-butyl acetophenone; cinnamonitrile; 5-phenyl-3-methyl-2-pentenoic acidnitrile; 5-phenyl-3-methylpentanoic acid nitrile; methyl anthranilate; methyl-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropyl quinoline; 6-isobutyl quinoline; 6-sec.-butyl quinoline; indole; skatole; 2-methoxy-3-isopropylpyrazine; 2-isobutyl-3-methoxypyrazine; the group comprising phenols, phenyl ethers and phenyl esters such as for example: estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;
the group comprising heterocyclic compounds such as for example: 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; the group comprising lactones such as for example: 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Surprisingly, it has been observed that the acetophenone derivatives of formula (I) using in compositions according to the present invention serve all the below mentioned needs simultaneously:

adjunction of acetophenone derivatives of formula (I) or a cosmetically or pharmaceutically acceptable salt thereof help solubilizing flavours and fragrances and/or lipophilic components in water-alcohol, preferably water-ethanol based formulations to obtain clear, transparent solutions. Without addition of said acetophenone derivatives of formula (I), the same formulation would be turbid and cloudy due to oil droplet formation of the flavours and fragrances and/or lipophilic components.

solubilizing flavours and fragrances and/or lipophilic components in water-based formulations to obtain clear, transparent solutions. Without addition of said acetophenone derivatives of formula (I), the same formulation would be turbid and cloudy due to oil droplet formation of the flavours and fragrances and/or lipophilic components.

to significantly counteracts malodour, such as body odour, specifically from sweat, furthermore malodour originating from kitchen, bathroom and smoke.

Therefore, acetophenone derivatives of formula (I) serve the need for so-called "true multitasking ingredients".

It has been surprisingly further observed that the acetophenone derivatives of formula (I), use alone or in a mixture of two or more acetophenone derivatives, also show the ability to stabilize emulsions through the improved solubility character of lipophilic compounds of the acetophenone derivatives of formula (I), especially o/w or w/o emulsions.

In a preferred embodiment of the above use, a composition according to the present invention comprises
a) at least one acetophenone derivative of formula (I):
in which

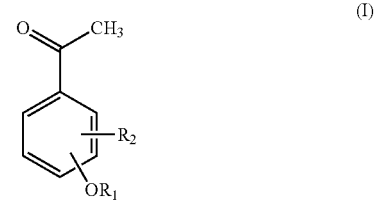

$R_1$ denotes hydrogen or methyl, and
$R_2$ denotes hydrogen, hydroxyl or a —OCH3 group,
or a cosmetically or pharmaceutically acceptable salt thereof, and
b) at least one flavour and/or fragrances and/or
c) at least one lipophilic component,
d) water,
and either
e) at least one emulsifier or surfactant and/or
f) at least one alcohol.

Suitable alcohols in the sense of the present invention are selected from ethanol, glycerol, propylenglycol, butylengylcol or mixture thereof.

In a preferred embodiment the above composition comprises
a) the acetophenone derivative of formula (I) is selected from the group consisting of: 2-hydroxyacetophenone, 3-hydroxyacetophenone, 4-hydroxyacetophenone and mixtures thereof,
b) the flavour and/or fragrance is selected from plant oils, synthetic or natural flavours and fragrances such as essential oils and flavours and fragrances on the basis of aldehydes, ketones, alcohols, ethers, esters, hydrocarbons and mixtures thereof,
c) the lipophilic component is selected from lipids, fatty acid esters, polymers, plant oils, neutral oils or any molecule which have lipophilic character.

In a preferred embodiment of the above use, the composition comprises a) at least one acetophenone derivative of formula (I):

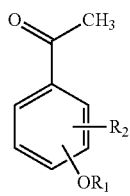

in which
$R_1$ denotes hydrogen or methyl, and
$R_2$ denotes hydrogen, hydroxyl or a —OCH3 group,
or a cosmetically or pharmaceutically acceptable salt thereof, and
b) at least one flavour and/or fragrances and/or
c) at least one lipophilic component,
d) water,
e) at least one emulsifier or surfactant.

In particular, the used composition of the present invention preferably comprises
(a) from 0.05 to 5% b.w. acetophenone derivatives of formula (I);
(b) from 0.05 to 5% b.w. flavours or fragrances,
(c) from 0.05 to 10% b.w. lipophilic components,
(d) from 50 to 99% b.w. water,
(e) from 0.5 to 25% b.w. emulsifiers or surfactants,
on condition that the amounts add—optionally together with additional ingredients—to 100% b.w.

In another preferred embodiment of the above use, the composition comprises
a) at least one acetophenone derivative of formula (I):

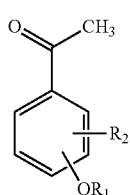

in which
$R_1$ denotes hydrogen or methyl, and
$R_2$ denotes hydrogen, hydroxyl or a —OCH3 group,
or a cosmetically or pharmaceutically acceptable salt thereof, and
b) at least one flavour and/or fragrances and/or
c) at least one lipophilic component,
d) water,
e) at least one alcohol.

In particular, the used composition of the present invention comprises
(a) from 0.05 to 5% b.w. acetophenone derivatives of formula (I);
(b) from 0.05 to 5% b.w. flavours or fragrances,
(c) from 0.05 to 5% b.w. lipophilic components,
(d) from 50 to 95% b.w. water,
(e) from 0.5 to 10% b.w. emulsifiers or surfactants,
(f) from 5 to 50% b.w. alcohols,
on condition that the amounts add—optionally together with additional ingredients—to 100% b.w.

The above used compositions are preferably used in cosmetic or pharmaceutical or household formulations, preferably as flavor or fragrance compositions.

Thus, a further object of the present invention relates to flavor and fragrance compositions comprising
a) at least one acetophenone derivative of formula (I)

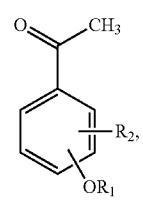

in which
$R_1$ denotes hydrogen or methyl, and
$R_2$ denotes hydrogen, hydroxyl or a —OCH3 group,
or a cosmetically or pharmaceutically acceptable salt thereof, and
b) at least a flavor and/or fragrance
and optionally
c) at least a lipophilic component.

The flavour and fragrance compositions of the present invention, preferably comprises
a) at least one acetophenone derivative of formula (I) as described above or a cosmetically or pharmaceutically acceptable salt thereof, and
b) at least one flavour and/or fragrances and/or
c) at least one lipophilic component,
d) water,
and either
e) at least one emulsifier or surfactant and/or
f) at least one alcohol,
wherein preferably
(i) the acetophenone derivative of formula (I) is selected from the group consisting of: 2-hydroxyacetophenone, 3-hydroxyacetophenone, 4-hydroxyacetophenone and mixtures thereof,
(ii) the flavour and/or fragrance is selected from plant oils, synthetic or natural flavours and fragrances such as flavours and fragrances on the basis of aldehydes, ketones, alcohols, ethers, esters, hydrocarbons and mixtures thereof,
(iii) the lipophilic component is selected from lipids, fatty acid esters, polymers, plant oils, neutral oils or any molecule which have lipophilic character.

In a preferred embodiment the flavor or fragrance composition comprises
(a) from 0.05 to 5% b.w. acetophenone derivatives of formula (I);
(b) from 0.05 to 5% b.w. flavours or fragrances,
(c) from 0.05 to 10% b.w. lipophilic components,
(d) from 50 to 99% b.w. water,
(e) from 0.5 to 25% b.w. emulsifiers or surfactants,
(f) from 5 to 50% b.w. alcohols,
on condition that the amounts add—optionally together with additional ingredients—to 100% b.w.

Acetophenone Derivatives

Acetophenone derivatives according to the present invention represent known compounds that can be obtained by ordinary methods of organic chemistry. It is understood that both substituents $OR_1$ and $R_2$ can be located in ortho, meta or para position towards the methylketo group.

Preferably, the species are selected from the group consisting of

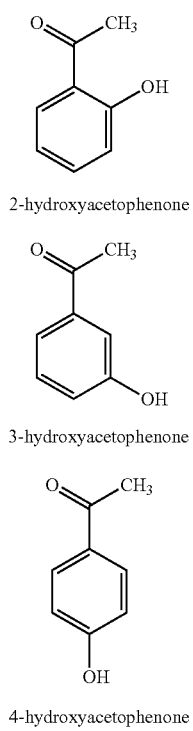

2-hydroxyacetophenone (Ia)

3-hydroxyacetophenone (Ib)

4-hydroxyacetophenone (Ic)

or their mixtures. In as far the definition refers to cosmetically or pharmaceutically acceptable salts of said derivatives, this means that these salts can be safely used for pharmaceutical purposes. This does not mean that the present invention or any aspect thereof is restricted to the use of a compound of formula (I) or a corresponding mixture for pharmaceutical purposes. Generally, if a salt can be used for pharmaceutical purposes it can likewise be used for cosmetic purposes, or in food or beverage formulations. In particular, the sodium and potassium and ammonium salts of compounds of formula (I) are considered as (pharmaceutically) acceptable salts. In some cases the utilization of the respective ionic compound or solvate carrier proves to be superior to the unmodified derivative. The (pharmaceutically) acceptable salts (and the corresponding solvates) of compounds of formula (I) can be prepared by standard procedures. Hereinafter, any reference to a compound of formula (I) or a corresponding mixture as defined above is to be understood as comprising an additional reference to corresponding (pharmaceutically) acceptable salts thereof.

In a preferred embodiment the used compositions and the flavour and fragrance compositions according to the present invention comprise or contain at least one, two or three of the compounds (Ia), (Ib) and (Ic), as for example 2-hydroxyacetophenone and 3-hydroxyacetophenone, or 2-hydroxyacetophenone and 4-hydroxyacetophenone, or 3-hydroxyacetophenone and 4-hydroxyacetophenone.

Cosmetical and Pharmaceutical Compositions

Another embodiment of the present invention covers personal care compositions, especially cosmetical compositions and furthermore pharmaceutical compositions comprising a working amount of derivatives of formula (I), respectively the flavour composition thereof.

The total amount of all acetophenone derivatives of formula (I) in such compositions are preferably from 0.05 wt.-% to 5 wt.-%, more preferably 0.5 wt.-% to 2 wt. %, most preferred 0.1 wt.-% to 1 wt.-%, calculated on the final cosmetical or pharmaceutical composition.

In an preferred embodiment such a cosmetic composition comprises
(a) from 0.05 to 5% b.w. acetophenone derivatives of formula (I);
(b) from 0.05 to 5% b.w. flavouring agents,
(c) from 0.05 to 10% b.w. lipophilic components,
(d) from 50 to 99% b.w. water,
(e) from 0.5 to 25% b.w. emulsifiers or surfactants,
(f) from 5 to 50% b.w. alcohol,
and optionally additionally
(g) from 50 to 99.9% b.w. oil bodies and/or waxes;
(h) 0 to about 25% b.w. active principles;
on condition that the amounts add—optionally together with additional ingredients—to 100% b.w.

The cosmetic and pharmaceutical compositions of the present invention may contain various further ingredients, which are usable for the intended use. Such as abrasives, antiacne agents, agents against ageing of the skin, anticellulitis agents, antidandruff agents, anti-inflammatory agents, irritation-preventing agents, irritation-inhibiting agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives and the like as additional auxiliaries and additives.

However, every named (cosmetic, pharmaceutical, household) composition (or formulation) may further comprise various further ingredients, additives and auxiliaries. Some of them maybe use in cosmetic and pharmaceutical formulations and compositions as well as in household products and compositions/formulations. For some of the ingredients, additives and auxiliaries, there are no precise divisions which of them are only used in one kind of composition or formulation. Thus, a series of ingredients, additives and auxiliaries can be used in cosmetic and pharmaceutical formulations and compositions as well as in the household products and compositions/formulations as needed. The below listings of the ingredients, additives and auxiliaries are therefore not only limited to the named compositions/ formulations underneath they are specified to.

A. Surfactants

Other preferred auxiliaries and additives are anionic and/ or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

B. Oil Bodies

Suitable oil bodies, which form constituents of the 0/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

C. Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

(i) Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

(ii) Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(iii) Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

(iv) Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

(v) Amphoteric emulsifiers. Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethylN-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

D. Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

E. Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

F. Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

G. Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

H. Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

I. Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

J. Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®MS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium)benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor
N-[(2 and 4)-[2-(oxoborn-3-ylidene)methyl]benzyl]acrylamide polymer
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4"-(1,3,5-triazine-2,4,6-triyl-triimino)tribenzoate (=2,4,6-trianilino-(p-carbo-2'-ethylhexyl-r-oxy)-1,3,5-triazine) (Uvinul®T150)

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxanyl)propyl) (Mexoryl®XL)
2,2'-methylene bis-(6-(2H-benzotriazol-2-yl)-4-1,1,3,3-tetramethylbutyl) phenol) (Tinosorb®M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methylpropyloxy)-2-hydroxy}phenyl]-6-(4-methoxyphenyl)-1,3,5-triazine UV-A filters which are preferably combined with one or more compounds of formula (I) in a preparation according to the present invention are selected from the group consisting of
4-isopropyl dibenzoyl methane
terephthalylidene dibornane sulfonic acid and salts (Mexoryl®SX)
4-t-butyl-4'-methoxydibenzoyl methane (avobenzone)/ (Neo Heliopan®357)
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
2-(4-diethylamino-2-hydroxybenzoyl)benzoic acid hexyl ester (Uvinul® A Plus)
indanylidene compounds in accordance with DE 100 55 940 A1 (=WO 2002 038537 A1)

UV filters which are more preferably combined with one or more compounds of formula (I) in a preparation according to the present invention are selected from the group consisting of
p-aminobenzoic acid
3-(4'-trimethylammonium)benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine (Tinosorb®S)

benzylidene malonate polysiloxane (Parsol®SLX)

menthyl anthranilate (Neo Heliopan®MA)

2-(4-diethylamino-2-hydroxybenzoyl)benzoic acid hexyl ester (Uvinul® A Plus)

indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

H. Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

J. Anti-Ageing Actives

In the context of the invention, anti-ageing or biogenic agents are, for example antioxidants, matrix-metalloproteinase inhibitrors (MMPI), skin moisturizing agents, glycosaminglycan stimulkators, anti-inflammatory agents, TRPV1 antagonists and plant extracts.

(i) Antioxidants. amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to μmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

(ii) Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonyl-fluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

(III) Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

(iv) Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

(v) Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*; preferably selected from the group consisting of extracts or fractions from camomile, Aloe vera, oats, calendula, arnica, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

(vi) TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

(vii) Botanical extracts. The compositions may also contain various extracts of plants, such as for example extracts of *Ginkgo biloba, Oleacea europensis, Glyzyrrhiza glabra, Vaccinium myrtillus, Trifolium pratense, Litchi sinensis, Vitis, vinifera, Brassica oleracea, Punica granatum, Petroselinium crispum, Centella asiatica, Passiflora incarnata, Medicago sativa, Melissa officinalis, Valeriana officinalis, Castanea sativa, Salix alba* and *Hapagophytum procumbens*.

K. Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, l-menthyl-methylether), menthylesters (for example menthylformiate, menthylacetate, menthylisobutyrate, menthyllactates, L-menthyl-L-lactate, L-menthyl-D-lactate, menthyl-(2-methoxyl)acetate, menthyl-(2-methoxyethoxyl) acetate, menthylpyroglutamate), menthylcarbonates (for example menthylpropyleneglycolcarbonate, menthylethyleneglycolcarbonate, menthylglycerolcarbonate or mixtures thereof), the semiesters of menthols with a dicarboxylic acid or derivatives thereof (for example monomenthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(–)-isopulegol, l-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

L. Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

M. Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

N. Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclo-hexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

O. Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

P. Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Q. Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

R. Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3Fe_3O_4$, FeO (OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or postfoaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

S. Fragrances, Flavours and Aroma Compounds

Fragrances, flavours and aroma compounds are well known in the art can be added to the compositions of the invention. The Fragrances, flavours and aroma compounds may be obtained from natural sources or prepared by organic synthesis. According to the present invention the terms "fragrances, flavours and aroma compounds" are herewith used equivalent to each.

Flavours and fragrances can be chosen from synthetic flavouring liquid and/or oils derived from plants leaves, flowers, fruits and so forth, and combinations thereof. Representative flavouring liquids include: artificial, natural or synthetic fruit flavours such as *eucalyptus*, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavours and fragrances are preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavour and fragrance compositions according to the invention comprise at least one flavour and/or fragrance, preferably two, three, four, five, six, seven, eight or more flavours and/or fragrances chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred flavours and fragrances encompass menthol, cineol, eugenol, thymol, cinnamic aldehyde, peppermint oil, spearmint oil, eucalyptus oil, thyme oil, cinnamon oil, clove oil, spruce needle oil, fennel oil, sage oil, aniseed oil, star anise oil, chamomile oil, and caraway oil, and their mixtures.

Typically, the synthetic fragrances and flavours represent aldehydes, ketones, alcohols, ethers, esters, hydrocarbons their mixtures. In the following these types of flavours and fragrances are illustrated but not limited by examples:

S.1 Aldehydes

Examples for suitable flavours and fragrances showing an aldehyde structure encompass melonal, triplal, ligustral, adoxal, anisaldehyde, cymal, ethylvanillin, florhydral, floralozon, helional, heliotropin, hydroxycitronellal, koavon, laurinaldehyde, canthoxal, lyral, lilial, adoxal, anisaldehyde, cumal, methyl-nonyl-acetaldehyde, citronellal, citronellyloxy-acetaldehyde, cyclamenaldehyde, bourgeonal, p-tert.-bucinal, phenylacetaldehyde, undecylenaldehyde, vanillin; 2,6,10-trimethyl-9-undecenal, 3-dodecen-1-al, α-n-Amylzimtaldehyde, 4-methoxy-benz-aldehyde, benzaldehyde, 3-(4-tert-butylphenyl)-propanal, 2-methyl-3-(paramethoxy-phe-nylpropanal), 2-methyl-4-(2,6,6-trimethyl-2(1)-cyclohexen-1-yl)butanal, 3-phenyl-2-pro-penal, cis-/trans-3,7-dimethyl-2,6-octadien-l-al, 3,7-dimethyl-6-octen-l-al,[(3,7-dimethyl-6-octenyl)-xy]-cetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxyaldehyde, 2-methyl-3-(isopropyl-phenyl)propanal, decyl aldehyde, 2,6-dimethyl-5-heptenal; 4-(tricyclo[5.2.1.0(2,6)]-decylidene-8)-butanal; octahydro-4,7-methano-IH-indenecarboxaldehyde; 3-ethoxy-4-hydroxybenzaldehyde, para-ethyl-alpha,alpha-dimethylhydrozimtaldehyde, α-methyl-3,4-(methylenedioxy)-hydrocinnamaldehyde, 3,4-methylenedioxybenzaldehyde, α-n-hexylcinnamaldehyde, m-cymene-7-carboxaldehyde, α-methylphenylacetaldehyde, 7-hydroxy-3,7-dimethyl octanal, undecenal, 2,4,6-trimethyl-3-cyclohexene-1-carboxalde-hyde, 4-(3)(4-methyl-3-pentenyl)-3-cyclohexen-carboxaldehyde, 1-dodecanal, 2,4-dimethyl-cyclohexene-3-ca rboxaldehyde, 4-(4-hydroxy-4-methylpentyl)-3-cylohexene-l-carboxal-dehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, 3-(4-ethylphenyl)-2,2-dimethylpropanal, 3-(4-methoxyphenyl)-2-methylpropanal, methylno-nylacetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methyl-propanal, 3-(3,4-Methylendioxyphenyl)-2-methylpropan-1-al, 3-(4-Ethylphenyl)-2,2-dimethylpropanal, 3-(3-Isopropylphenyl)-butan-1-al, 2,6-Dimethylhept-5-en-1-al, Dihydrozimtaldehyde, 1-methyl-4-(4-methyl-3-pentenyl)-3-cyclohexene-1-carboxaldehyde, 5- or 6-Methoxyhexahydro-4,7-methanoindan-1 or 2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexene-carboxyaldehyde, 7-hydroxy-3,7-dimethyl-octanal; trans-4-decenal, 2,6-nonadienal, p-tolylacetaldehyde; 4-methylphenylacetaldehyde, 2-methyl-4-(2,6,6-trimethyl-1-cyclohexen-1-yl)-2-butenal, o-methoxyzimtaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindan-1-carboxaldehyde, octanal, 2-methyl octanal, alpha-methyl-4-(l-methylethyl)benzene-acetaldehyde, 6,6-dimethyl-2-norpinene-2-propionaldehyde, p-methyl phenoxy acetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, 1-p-menthene-q-carboxaldehyde, citral or its mixtures, lilial citral, 1-decanal, n-undecanal, n-dodecanal, hlorhydral, 2,4-dimethyl-3-cyclohexen-1-carboxaldehyde 4-methoxybenzaldehyde, 3-methoxy-4-hydroxy-benzalde-hyde, 3-ethoxy-4-hydroxybenzaldehyde, 3,4-methylendioxybenzaldehyde, 3,4-dimethoxybenzaldehyde and their mixtures.

As explained above, said ketones or said aldehydes may show an aliphatic, cycloaliphatic, aromatic, ethylenically unsaturated structure or a mixture of these elements. The components may also include heteroatoms or show a polycyclic structure. Suitable substituents for all these structures are hydroxyl and/or amino groups. Further fragrances are compiled in the following document: *Steffen Arctander* "Published 1960 and 1969 respectively, Re-printed2000 ISBN: Aroma Chemicals Vol. 1: 0-931710-37-5, Aroma Chemicals Vol. 2: 0-931710-38-3", which is hereby incorporated by reference.

S.2 Ketones

Examples for suitable flavours and fragrances showing a ketone structure encompass buccoxime, iso jasmone, methyl beta naphthyl ketone, moschus indanone, tonalid/moschus plus, α-damascone, β-damascon, δ-damascone, Iso-damascone, damascenone, damarose, methyl-dihydrojasmonate, menthone, carvone, campher, fenchone, alphalonen, β-iononw, dihydro-β-lonone, γ-methylionone, fleuramone, dihydrojasmone, cis-Jasmon, iso-E-Super, methyl cedrenylk etone, or methyl cedrylon, acetophenone, methyl aceto phenone, p-methoxyacetophenone, methyl-β-naphtyl ketone, benzylacetone, benzophenone, p-hydroxy phenylbutanone, celery Ketone or livescon, 6-osopropyl-deca-hydro-2-naphtone, dimethyloctenone, freskomenth, 4-(l-ethoxyvinyl)-3,3,5,5,-tetramethylv cyclohexanone, methylheptenone, 2-(2-(4-Methyl-3-cyclohexen-1-yl)propyl)-cyclopentanone, 1-(p-men-thene-6(2)-yl)-1-propanone, 4-(4-Hydroxy-3-methoxyphenyl)-2-butanone, 2-Acetyl-3,3-di-methyl-norbornan, 6,7-dihydro-1,1,2,3,3-pentamethyl-4(5H)-indanone, 4-damascol, dulcinyl or cassione, gelsone, hexalone, isocyclemone E, Methylcyclocitrone, methyl lavender ketone, orivone, p-tert-butyl cyclohexanone, verdone, delphone, muscone, neobutenone, plicatone, veloutone, 2,4,4,7-tetramethyl-oct-6-en-3-one, tetrameran, hedion and their mixtures. The preferred ketones are selected from the group comprising α-damascone, δ-damascone, iso-damascone, carvone, γ-methyl ionone, Iso-E-Super, 2,4,4,7-tetramethyl-oct-6-en-3-one, benzylacetone, 3-damascone, damascenone, methyl dihydrojasmonate, methyl cedrylone, hedione and their mixtures S.3 Alcohols Suitable flavour and fragrance alcohols encompass for example 10-undecen-1-ol, 2,6-dimethylheptan-2-ol, 2-methylbutanol, 2-methylpentanol, 2-phenoxyethanol, 2-phenylpropanol, 2-tert-Butycyclohexanol, 3,5,5-trimethylcyclohexanol, 3-hexanol, 3-methyl-5-phenylpentanol, 3-octanol, 1-octen-3-ol, 3-phenylpropanol, 4-heptenol, 4-isopropylcyclohexanol, 4-tert-butycyclohexanol, 6,8-dimethyl-2-nonanol, 6-nonen-1-ol, 9-decen-1-ol, α-methyl benzylalcohol, α-terpineol, amylsalicylat, benzyl alcohol, benzyl salicylate, 3-terpineol, butyl salicylate, citronellol, cyclohexyl salicylate, decanol, dihydromyrcenol, dimethyl benzylcarbinol, dimethyl heptanol, dimethyl octanol, ethyl salicylate, ethyl vanilin, anethol, eugenol, geraniol, heptanol, hexyl salicylat, isoborneol, isoeugenol, isopulegol, linalool, menthol, myrtenol, n-hexanol, nerol, nonanol, octanol, para-menthan-7-ol, phenylethylalkohol, phenol, phenyl salicylat, tetrahydro geraniol, tetrahydro linalool, thymol, trans-2-cis-6-nonadienol, trans-2-nonen-1-ol, trans-2-octenol, undecanol, vanillin, cinnamalcohol and their mixtures.

S.4 Esters

Examples for suitable flavours and fragrances showing a ketone structure encompass benzyl acetate, phenoxyisobutyrate, p-tert.-butylcyclohexylacetate, linalylacetate, dimethylbenzyl-carbinylacetate (DMBCA), phenylethylacetate, benzylacetate, ethylmethylphenylglycinate, allylcyclohexylpropionate, styrallylpropionate, benzylsalicylate, cyclohexylsalicylate, floramat, melusat, jasmacyclatat and their mixtures.

S.5 Ethers

Examples for suitable flavours and fragrances showing a ketone structure encompass benzylethyl ether or ambroxan S.6 Perfume Oils Suitable flavours and fragrances may also be on the base of perfume oils, which are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxy-acetaldehyde, cyclamen aldehyde, hydroxycitronellal, lilial and bourgeonal. Examples of suitable ketones are the ionones, ?-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and flora mat.

Household Compositions

Another embodiment of the present invention covers household compositions, such as detergent compositions comprising a working amount of at least one acetophenone derivative of formula (I) and at least one flavour and/or fragrance and/or lipophilic component, water and either at least one emulsifier or surfactant and/or at least one alcohol.

The total amount of all acetophenone derivatives of formula (I) in such a composition is preferably from 0.05 wt.-% to 5 wt.-%, more preferably 0.5 wt.-% to 2 wt.-%, and most preferred from 0.1 wt.-% to 1 wt.-% calculated on the final household composition. The total amount of all flavours and/or fragrances or lipophilic components in household compositions is preferably in the range from 0.05% b.w. to 10% b.w. more preferably 0.1 wt.-% to 5 wt.-%, and most preferred from 0.1 wt.-% to 2 wt.-% calculated on the final household composition based on the total amount of the final household composition.

The household compositions according to the present invention may comprise further customarily additives, auxiliaries and ingredients such as, for example, anionic, nonionic, cationic, amphoteric or zwitterionic (co-)surfactants, organic solvents, builders, enzymes, soil repellents, thickeners, colorants and foam inhibitors and the like.

A. Anionic (Co-) Surfactants

Preferably, surfactants of the sulfonate type, alk(en)yl sulfonates, alkoxylated alk(en)yl sulfates, ester sulfonates and/or soaps are used as the anionic surfactants. Suitable surfactants of the sulfonate type are advantageously $C_{9-13}$ alkylbenzene sulfonates, olefin sulfonates, i.e. mixtures of alkene- and hydroxyalkane sulfonates, and disulfonates, as are obtained, for example, by the sulfonation with gaseous sulfur trioxide of $C_{12-18}$ monoolefins having a terminal or internal double bond and subsequent alkaline or acidic hydrolysis of the sulfonation products.

(i) Alk(en)yl sulfates. Preferred alk(en)yl sulfates are the alkali and especially the sodium salts of the sulfuric acid half-esters of the $C_{12}$-$C_{18}$ fatty alcohols, for example, from coconut butter alcohol, tallow alcohol, lauryl, myristyl, cetyl or stearyl alcohol or from $C_8$-$C_{20}$ oxo alcohols and those half-esters of secondary alcohols of these chain lengths. Alk(en)yl sulfates of the cited chain lengths that comprise a synthetic straight chain alkyl group manufactured petrochemically are also preferred. The $C_{12}$-$C_{16}$ alkyl sulfates and $C_{12}$-$C_{15}$ alkyl sulfates as well as $C_{14}$-$C_{15}$ alkyl sulfates and $C_{14}$-$C_{16}$ alkyl sulfates are particularly preferred on the grounds of laundry performance. The 2,3-alkyl sulfates, which can be obtained from Shell Oil Company under the trade name DAN™, are also suitable anionic surfactants.

(ii) Alk(en)yl ether sulfates. Sulfuric acid mono-esters derived from straight-chained or branched $C_7$-$C_{21}$ alcohols ethoxylated with 1 to 6 moles ethylene oxide are also suitable, such as 2-methyl-branched $C_9$-$C_{11}$ alcohols with an average of 3.5 mol ethylene oxide (EO) or $C_{12}$-$C_{18}$ fatty alcohols with 1 to 4 EO.

(iii) Ester sulfonates. The esters of alpha-sulfo fatty acids (ester sulfonates), e.g., the alpha-sulfonated methyl esters of hydrogenated coco-, palm nut- or tallow acids are likewise suitable.

(iv) Soaps. Soaps, in particular, can be considered as further anionic surfactants. Saturated fatty acid soaps are particularly suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid. Those soap mixtures are particularly preferred that are composed of 50 to 100 wt. % of saturated $C_{12}$-$C_{24}$ fatty acid soaps and 0 to 50 wt. % of oleic acid soap.

(v) Ether carboxylic acids. A further class of anionic surfactants is that of the ether carboxylic acids, obtainable by treating fatty alcohol ethoxylates with sodium chloroacetate in the presence of basic catalysts. They have the general formula: $RO(CH_2CH_2O)_pCH_2COOH$ with $R=C_1$-$C_{18}$ and p=0.1 to 20. Ether carboxylic acids are insensitive to water hardness and possess excellent surfactant properties.

B. Nonionic (Co-)Surfactants (i) Alkohol alkoxylates. The added nonionic surfactants are preferably alkoxylated and/or propoxylated, particularly primary alcohols having preferably 8 to 18 carbon atoms and an average of 1 to 12 mol ethylene oxide (EO) and/or 1 to 10 mol propylene oxide (PO) per mol alcohol. $C_8$-$C_{16}$-Alcohol alkoxylates, advantageously ethoxylated and/or propoxylated $C_{10}$-$C_{15}$-alcohol alkoxylates, particularly $C_{12}$-$C_{14}$ alcohol alkoxylates, with an ethoxylation degree between 2 and 10, preferably between 3 and 8, and/or a propoxylation degree between 1 and 6, preferably between 1.5 and 5, are particularly preferred. The cited degrees of ethoxylation and propoxylation constitute statistical average values that can be a whole or a fractional number for a specific product. Preferred alcohol ethoxylates and propoxylates have a narrowed homolog distribution (narrow range ethoxylates/propoxylates, NRE/NRP). In addition to these nonionic surfactants, fatty alcohols with more than 12 EO can also be used. Examples of these are (tallow) fatty alcohols with 14 EO, 16 EO, 20 EO, 25 EO, 30 EO or 40 EO.

(ii) Alkylglycosides (APG®). Furthermore, as additional nonionic surfactants, alkyl glycosides that satisfy the general Formula $RO(G)_x$, can be added, e.g., as compounds, particularly with anionic surfactants, in which R means a primary linear or methyl-branched, particularly 2-methyl-branched, aliphatic group containing 8 to 22, preferably 12 to 18 carbon atoms and G stands for a glycose unit containing 5 or 6 carbon atoms, preferably for glucose. The degree of oligomerization x, which defines the distribution of monoglycosides and oligoglycosides, is any number between 1 and 10, preferably between 1.1 and 1.4.

(iii) Fatty acid ester alkoxylates. Another class of preferred nonionic surfactants, which are used either as the sole nonionic surfactant or in combination with other nonionic surfactants, in particular, together with alkoxylated fatty alcohols and/or alkyl glycosides, are alkoxylated, preferably ethoxylated or ethoxylated and propoxylated fatty acid alkyl esters preferably containing 1 to 4 carbon atoms in the alkyl chain, more particularly the fatty acid methyl esters which are described, for example, in Japanese Patent Application JP-A-58/217598 or which are preferably produced by the process described in International Patent Application WO-A-90/13533. Methyl esters of $C_{12}$-$C_{18}$ fatty acids containing an average of 3 to 15 EO, particularly containing an average of 5 to 12 EO, are particularly preferred.

(iv) Amine oxides. Nonionic surfactants of the amine oxide type, for example, N-coco alkyl-N,N-dimethylamine oxide and N-tallow alkyl-N,N-dihydroxyethylamine oxide, and the fatty acid alkanolamides may also be suitable. The quantity in which these nonionic surfactants are used is preferably no more than the quantity in which the ethoxylated fatty alcohols are used and, particularly no more than half that quantity.

(v) Gemini surfactants. The so-called gemini surfactants can be considered as further surfactants. Generally speaking, such compounds are understood to mean compounds that have two hydrophilic groups and two hydrophobic groups per molecule. As a rule, these groups are separated from one another by a "spacer". The spacer is usually a hydrocarbon chain that is intended to be long enough such that the hydrophilic groups are a sufficient distance apart to be able to act independently of one another. These types of surfactants are generally characterized by an unusually low critical micelle concentration and the ability to strongly reduce the surface tension of water. In exceptional cases, however, not only dimeric but also trimeric surfactants are meant by the term gemini surfactants. Suitable gemini surfactants are, for example, sulfated hydroxy mixed ethers according to German Patent Application DE 4321022 A1 or dimer alcohol bis- and trimer alcohol tris sulfates and ether sulfates according to International Patent Application WO 96/23768 A1. Blocked end group dimeric and trimeric mixed ethers according to German Patent Application DE 19513391 A1 are especially characterized by their bifunctionality and multifunctionality. Gemini polyhydroxyfatty acid amides or polyhydroxyfatty acid amides, such as those described in International Patent Applications WO 95/19953 A1, WO 95/19954 A1 and WO 95/19955 A1 can also be used.

C. Cationic Co-Surfactants (i) Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

(ii) Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternization of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

D. Amphoteric or Zwitterionic Co-Surfactants (i) Betaines. Amphoteric or ampholytic surfactants possess a plurality of functional groups that can ionize in aqueous solution and thereby—depending on the conditions of the medium—lend anionic or cationic character to the compounds (see DIN 53900, July 1972). Close to the isoelectric point (around pH 4), the amphoteric surfactants form inner salts, thus becoming poorly soluble or insoluble in water. Amphoteric surfactants are subdivided into ampholytes and betaines, the latter existing as zwitterions in solution. Ampholytes are amphoteric electrolytes, i.e. compounds that possess both acidic as well as basic hydrophilic groups and therefore behave as acids or as bases depending on the conditions. Especially betaines are known surfactants which are mainly produced by carboxyalkylation, preferably carboxymethylation, of amine compounds. The starting materials are preferably condensed with halocarboxylic acids or salts thereof, more particularly sodium chloroacetate, one mole of salt being formed per mole of betaine. The addition of unsaturated carboxylic acids, such as acrylic acid for example, is also possible. Examples of suitable betaines are the carboxy alkylation products of secondary and, in particular, tertiary amines which correspond to formula $R^1R^2R^3N$—$(CH_2)_qCOOX$ where $R^1$ is a an alkyl radical having 6 to 22 carbon atoms, $R^2$ is hydrogen or an alkyl group containing 1 to 4 carbon atoms, $R^3$ is an alkyl group containing 1 to 4 carbon atoms, q is a number of 1 to 6 and X is an alkali and/or alkaline earth metal or ammonium. Typical examples are the carboxymethylation products of hexylmethylamine, hexyldimethylamine, octyldimethylamine, decyldimethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and their technical mixtures, and particularly dodecyl methylamine, dodecyl dimethylamine, dodecyl ethylmethylamine and technical mixtures thereof.

(ii) Alkylamido betaines. Other suitable betaines are the carboxyalkylation products of amidoamines corresponding to formula $R^1CO(R^3)(R^4)$—NH—$(CH_2)_p$—N—$(CH_2)_qCOOX$ in which $R^1CO$ is an aliphatic acyl radical having 6 to 22 carbon atoms and 0 or 1 to 3 double bonds, $R^2$ is hydrogen or an alkyl radical having 1 to 4 carbon atoms, $R^3$ is an alkyl radical having 1 to 4 carbon atoms, p is a number from 1 to 6, q is a number from 1 to 3 and X is an alkali and/or alkaline earth metal or ammonium. Typical examples are reaction products of fatty acids having 6 to 22 carbon atoms, like for example caproic acid, caprylic acid, caprinic acid, lauric acid, myristic acid, palmitic acid, palmoleic acid, stearic acid, isostearic acid, oleic acid, elaidic acid, petroselinic acid, linolic acid linoleic acid, elaeostearic acid, arachidonic acid, gadoleic acid, behenic acid, erucic acid and their technical mixtures with N,N-dimethylaminoethylamine, N,N-dimethylaminopropylamine, N,N-diethylaminoethylamine and N,N-diethylaminopropylamine, which are condensed with sodium chloroacetate. The commercially available products include Dehyton® K and Dehyton® PK (Cognis Deutschland GmbH & Co., KG) as well as Tego®Betaine (Goldschmidt).

(iii) Imidazolines. Other suitable starting materials for the betaines to be used for the purposes of the invention are imidazolines. These substances are also known and may be obtained, for example, by cyclizing condensation of 1 or 2 moles of $C_6$-$C_{22}$ fatty acids with polyfunctional amines, such as for example aminoethyl ethanolamine (AEEA) or diethylenetriamine. The corresponding carboxyalkylation products are mixtures of different open-chain betaines. Typical examples are condensation products of the above-mentioned fatty acids with AEEA, preferably imidazolines based on lauric acid, which are subsequently betainised with sodium chloroacetate. The commercially available products include Dehyton® G (Cognis Deutschland GmbH & Co., KG)

The amount of (co-)surfactant comprised in the inventive compositions is advantageously 0.1 wt. % to 90 wt. %, particularly 10 wt. % to 80 wt. % and particularly preferably 20 wt. % to 70 wt.-%.

E. Organic Solvents

Liquid light or heavy duty detergents may comprise organic solvents, preferably those miscible with water. Polydiols, ethers, alcohols, ketones, amides and/or esters are preferably used as the organic solvent for this in amounts of 0 to 90 wt. %, preferably 0.1 to 70 wt. %, particularly 0.1 to 60 wt. %. Low molecular weight polar substances, such as for example, methanol, ethanol, propylene carbonate, acetone, acetonylacetone, diacetone alcohol, ethyl acetate, 2-propanol, ethylene glycol, propylene glycol, glycerin, diethylene glycol, dipropylene glycol monomethyl ether and dimethylformamide or their mixtures are preferred.

F. Enzymes

Suitable enzymes include, in particular, those from the classes of hydrolases, such as proteases, esterases, lipases or lipolytic enzymes, amylases, cellulases or other glycosyl hydrolases and mixtures thereof. In the wash, all these hydrolases contribute to removing stains such as protein, fat or starchy stains and against graying. Moreover, cellulases and other glycosyl hydrolases can contribute to increased softness of the textile and to color retention by removing pilling and micro fibrils. Oxidoreductases can also be added to the bleaches or to inhibit the color transfer. Enzymatic active materials obtained from bacterial sources or fungi such as *Bacillus subtilis, Bacillus licheniformis, Streptomyceus griseus* and *Humicola insolens* are particularly well suited. Proteases of the subtilisin type and particularly proteases that are obtained from *Bacillus lentus* are preferably used. Here, mixtures of enzymes are of particular interest, for example, proteases and amylases or proteases and lipases or lipolytic enzymes or proteases and cellulases or cellulases and lipase or lipolytic enzymes or proteases, amylases and lipases or lipolytic enzymes or proteases, lipases or lipolytic enzymes and cellulases, in particular, however proteases and/or lipase-containing mixtures or mixtures with lipolytic enzymes. Examples of such lipolytic enzymes are the known cutinases. Peroxidases or oxidases have also proved to be suitable in certain cases. The suitable amylases particularly include .alpha.-amylases, iso-amylases, pullulanases and pectinases. Cellobiohydrolases, endoglucanases and .beta.-glucosidases or mixtures thereof, which are also known as cellobiases, are preferred cellulases. As the different cellulase types differ in their CMCase and avicelase activities, the required activities can be adjusted by controlled mixtures of the cellulases. The content of the enzymes or enzyme mixtures may be, for example, about 0.1 to 5% by weight and is preferably 0.1 to about 3% by weight.

G. Builders (i) Zeolites. Fine crystalline, synthetic zeolites containing bound water can be used as builders, for example, preferably zeolite A and/or P. Zeolite MAP® (commercial product of the Crosfield company), is particularly preferred as the zeolite P. However, zeolite X and mixtures of A, X, Y and/or P are also suitable. A co-crystallized sodium/potassium aluminum silicate from Zeolite A and Zeolite X, which is available as Vegobond® RX. (commercial product from Condea Augusta S.p.A.), is also of particular interest. Preferably, the zeolite can be used as a spray-dried powder. For the case where the zeolite is added as a suspension, this can comprise small amounts of nonionic surfactants as stabilizers, for example, 1 to 3 wt. %, based on the zeolite, of ethoxylated $C_{12}$-$C_{18}$ fatty alcohols with 2 to 5 ethylene oxide groups, $C_{12}$-$C_{14}$ fatty alcohols with 4 to 5 ethylene oxide groups or ethoxylated isotridecanols. Suitable zeolites have an average particle size of less than 10 μm (test method: volumetric distribution Coulter counter) and preferably comprise 18 to 22 wt. %, particularly 20 to 22 wt. % of bound water. Apart from this, phosphates can also be used as builders.

(ii) Layered silicates. Suitable substitutes or partial substitutes for phosphates and zeolites are crystalline, layered sodium silicates. These types of crystalline layered silicates are described, for example, in European Patent Application EP 0164514 A1. Preferred crystalline layered silicates are those obtained for example, from the process described in International Patent Application WO 91/08171 A1.

(iii) Amorphous silicates. Preferred builders also include amorphous sodium silicates with a modulus ($Na_2O$:$SiO_2$ ratio) of 1:2 to 1:3.3, preferably 1:2 to 1:2.8 and more preferably 1:2 to 1:2.6, which dissolve with a delay and exhibit multiple wash cycle properties. The delay in dissolution compared with conventional amorphous sodium silicates can have been obtained in various ways, for example, by surface treatment, compounding, compressing/compacting or by over-drying. In the context of this invention, the term "amorphous" also means "X-ray amorphous". In other words, the silicates do not produce any of the sharp X-ray reflexions typical of crystalline substances in X-ray diffraction experiments, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This is to be interpreted to mean that the products have microcrystalline regions between 10 and a few hundred nm in size, values of up to at most 50 nm and especially up to at most 20 nm being preferred. This type of X-ray amorphous silicates, which similarly possess a delayed dissolution in comparison with the customary water glasses, are described, for example, in German Patent Application DE 4400024 A1. Compacted/densified amorphous silicates, compounded amorphous silicates and over dried X-ray-amorphous silicates are particularly preferred.

(iv) Phosphates. Also the generally known phosphates can also be added as builders, in so far that their use should not be avoided on ecological grounds. The sodium salts of the orthophosphates, the pyrophosphates and especially the tripolyphosphates are particularly suitable. Their content is generally not more than 25 wt. %, preferably not more than 20 wt. %, each based on the finished composition. In some cases it has been shown that particularly tripolyphosphates, already in low amounts up to maximum 10 wt. %, based on the finished composition, in combination with other builders, lead to a synergistic improvement of the secondary washing power. Preferred amounts of phosphates are under 10 wt. %, particularly 0 wt. %.

H. Cobuilders (i) Polycarboxylic acids. Useful organic cobuilders are, for example, the polycarboxylic acids usable in the form of their sodium salts of polycarboxylic acids, wherein polycarboxylic acids are understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA) and its derivatives and mixtures thereof. Preferred salts are the salts of polycarboxylic acids such as citric acid, adipic acid, succinic acid, glutaric acid, tartaric acid, sugar acids and mixtures thereof.

(ii) Organic acids. Acids per se can also be used. Besides their building effect, the acids also typically have the property of an acidifying component and, hence also serve to establish a relatively low and mild pH in detergents or cleansing compositions. Citric acid, succinic acid, glutaric acid, adipic acid, gluconic acid and any mixtures thereof are particularly mentioned in this regard. Further suitable acidifiers are the known pH regulators such as sodium hydrogen carbonate and sodium hydrogen sulfate.

(iii) Polymers. Particularly suitable polymeric cobuilders are polyacrylates, which preferably have a molecular weight of 2,000 to 20,000 g/mol. By virtue of their superior solubility, preferred representatives of this group are again the short-chain polyacrylates, which have molecular weights of 2,000 to 10,000 g/mol and, more particularly, 3,000 to 5,000 g/mol. Suitable polymers can also include substances that consist partially or totally of vinyl alcohol units or its derivatives.

Further suitable copolymeric polycarboxylates are particularly those of acrylic acid with methacrylic acid and of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2,000 to 70,000 g/mol, preferably 20,000 to 50,000 g/mol and especially 30,000 to 40,000 g/mol. The (co)polymeric polycarboxylates can be added either as an aqueous solution or preferably as powder. In order to improve the water solubility, the polymers can also comprise allylsulfonic acids as monomers, such as, for example, allyloxybenzene sulfonic acid and methallyl sulfonic acid as in the EP 0727448 B1.

Biodegradable polymers comprising more than two different monomer units are particularly preferred, examples being those comprising, as monomers, salts of acrylic acid and of maleic acid, and also vinyl alcohol or vinyl alcohol derivatives, as in DE 4300772 A1, or those comprising, as monomers, salts of acrylic acid and of 2-alkylallyl sulfonic acid, and also sugar derivatives. Further preferred copolymers are those that are described in German Patent Applications DE 4303320 A1 and DE 4417734 A1 and preferably include acrolein and acrylic acid/acrylic acid salts or acrolein and vinyl acetate as monomers.

Similarly, other preferred builders are polymeric aminodicarboxylic acids, salts or precursors thereof. Those polyaspartic acids or their salts and derivatives disclosed in German Patent Application DE 19540086 A1 as having a bleach-stabilizing action in addition to cobuilder properties are particularly preferred.

Further suitable builders are polyacetals that can be obtained by treating dialdehydes with polyol carboxylic acids that possess 5 to 7 carbon atoms and at least 3 hydroxyl groups, as described in European Patent Application EP 0280223 A1. Preferred polyacetals are obtained from dialdehydes like glyoxal, glutaraldehyde, terephthalaldehyde as well as their mixtures and from polycarboxylic acids like gluconic acid and/or glucoheptonic acid.

(iv) Carbohydrates. Further suitable organic cobuilders are dextrins, for example, oligomers or polymers of carbohydrates that can be obtained by the partial hydrolysis of starches. The hydrolysis can be carried out using typical processes, for example, acidic or enzymatic catalyzed processes. The hydrolysis products preferably have average molecular weights in the range of 400 to 500,000 g/mol. A polysaccharide with a dextrose equivalent (DE) of 0.5 to 40 and, more particularly, 2 to 30 is preferred, the DE being an accepted measure of the reducing effect of a polysaccharide in comparison with dextrose, which has a DE of 100. Both maltodextrins with a DE between 3 and 20 and dry glucose syrups with a DE between 20 and 37 and also so-called yellow dextrins and white dextrins with relatively high molecular weights of 2,000 to 30,000 g/mol may be used. A preferred dextrin is described in British Patent Application 94 19 091.

The oxidized derivatives of such dextrins concern their reaction products with oxidizing compositions that are capable of oxidizing at least one alcohol function of the saccharide ring to the carboxylic acid function. Such oxidized dextrins and processes for their manufacture are known for example, from European Patent Applications EP 0232202 A1. A product oxidized at C6 of the saccharide ring can be particularly advantageous.

(v) Oxydisuccinates and other derivatives of disuccinates, preferably ethylenediamine disuccinate are also further suitable cobuilders. Here, ethylene diamine-N,N'-disuccinate (EDDS), the synthesis of which is described for example, in U.S. Pat. No. 3,158,615, is preferably used in the form of its sodium or magnesium salts. In this context, glycerine disuccinates and glycerine trisuccinates are also particularly preferred, such as those described in U.S. Pat. No. 4,524,009. Suitable addition quantities in zeolite-containing and/or silicate-containing formulations range from 3 to 15% by weight.

(vi) Lactones. Other useful organic co-builders are, for example, acetylated hydroxycarboxylic acids and salts thereof which optionally may also be present in lactone form and which contain at least 4 carbon atoms, at least one hydroxyl group and at most two acid groups. Such cobuilders are described, for example, in International Patent Application WO 95/20029 A1.

I. Soil Repellents

In addition, the compositions can also comprise components that positively influence the oil and fat removal from textiles during the wash (so-called soil repellents). This effect is particularly noticeable when a textile is dirty and had been previously already washed several times with an inventive detergent that comprised this oil- or fat-removing component. The preferred oil and fat removing components include, for example, nonionic cellulose ethers such as methyl cellulose and methyl hydroxypropyl cellulose with a content of methoxy groups of 15 to 30 wt. % and hydroxypropoxy groups of 1 to 15 wt. %, each based on the nonionic cellulose ether, as well as polymers of phthalic acid and/or terephthalic acid or their derivatives known from the prior art, particularly polymers of ethylene terephthalates and/or polyethylene glycol terephthalates or anionically and/or nonionically modified derivatives thereof. From these, the sulfonated derivatives of the phthalic acid polymers and the terephthalic acid polymers are particularly preferred.

J. Inorganic Salts

Further suitable ingredients of the composition are water-soluble inorganic salts such as bicarbonates, carbonates, amorphous silicates or mixtures of these; alkali carbonate and amorphous silicate are particularly used, principally sodium silicate with a molar ratio $Na_2O:SiO_2$ of 1:1 to 1:4.5, preferably of 1:2 to 1:3.5. Preferred compositions comprise alkaline salts, builders and/or cobuilders, preferably sodium carbonate, zeolite, crystalline, layered sodium silicates and/ or trisodium citrate, in amounts of 0.5 to 70 wt. %, preferably 0.5 to 50 wt. %, particularly 0.5 to 30 wt. % anhydrous substance.

K. Foam Inhibitors

Especially when used in automatic washing processes, it can be advantageous to add conventional foam inhibitors to the compositions. Suitable foam inhibitors include for example, soaps of natural or synthetic origin, which have a high content of $C_{18}$-$C_{24}$ fatty acids. Suitable non-surface-active types of foam inhibitors are, for example, organopolysiloxanes and mixtures thereof with microfine, optionally silanised silica and also paraffins, waxes, microcrystalline waxes and mixtures thereof with silanised silica or bis-stearyl ethylenediamide. Mixtures of various foam inhibitors, for example, mixtures of silicones, paraffins or waxes, are also used with advantage. Preferably, the foam inhibitors, especially silicone-containing and/or paraffin-containing foam inhibitors, are loaded onto a granular, water-soluble or dispersible carrier material. Especially in this case, mixtures of paraffins and bis-stearylethylene diamides are preferred.

L. Sequestrants

The salts of polyphosphonic acid can be considered as sequestrants or as stabilizers, particularly for peroxy compounds and enzymes, which are sensitive towards heavy metal ions. Here, the sodium salts of, for example, 1-hydroxyethane-1,1-diphosphonate, diethylenetriamine pentamethylene phosphonate or ethylenediamine tetramethylene phosphonate are used in amounts of 0.1 to 5 wt. %.

M. Graying Inhibitors

Graying inhibitors have the function of maintaining the dirt that was removed from the fibers suspended in the washing liquor, thereby preventing the dirt from resettling. Water-soluble colloids of mostly organic nature are suitable for this, for example, the water-soluble salts of (co)polymeric carboxylic acids, glue, gelatins, salts of ether carboxylic acids or ether sulfonic acids of starches or celluloses, or salts of acidic sulfuric acid esters of celluloses or starches. Water-soluble, acid group-containing polyamides are also suitable for this purpose. Moreover, soluble starch preparations and others can be used as the above-mentioned starch products, e.g., degraded starches, aldehyde starches etc. Polyvinyl pyrrolidone can also be used. Preference, however, is given to the use of cellulose ethers such as carboxymethyl cellulose (Na salt), methyl cellulose, hydroxyalkyl celluloses and mixed ethers such as methyl hydroxyethyl cellulose, methyl hydroxypropyl cellulose, methyl carboxymethyl cellulose and mixtures thereof, as well as polyvinyl pyrrolidone, which can be added, for example, in amounts of 0.1 to 5 wt. %, based on the composition.

N. Optical Brighteners and UV Adsorbers

The compositions may comprise e.g., derivatives of diaminostilbene disulfonic acid or alkali metal salts thereof as the optical brighteners. Suitable optical brighteners are, for example, salts of 4,4'-bis-(2-anilino-4-morpholino-1,3, 5-triazinyl-6-amino)stilbene-2,2'-di-sulfonic acid or compounds of similar structure which contain a diethanolamino group, a methylamino group, an anilino group or a 2-methoxyethylamino group instead of the morpholino group. Brighteners of the substituted diphenylstyryl type may also be present, for example, the alkali metal salts of 4,4'-bis(2-sulfostyryl)diphenyl, 4,4'-bis(4-chloro-3-sulfostyryl)diphenyl or 4-(4-chlorostyryl)-4'-(2-sulfostyryl) diphenyl. Mixtures of the mentioned brighteners may also be used.

In addition, UV absorbers may also be added. These are compounds with distinct absorption abilities for ultra violet radiation, which contribute as UV stabilizers as well as to improve the light stability of colorants and pigments both for textile fibers as well as for the skin of the wearer of textile products by protecting against the UV radiation that penetrates the fabric. In general, the efficient radiationless deactivating compounds are derivatives of benzophenone, substituted with hydroxyl and/or alkoxy groups, mostly in position(s) 2 and/or 4. Also suitable are substituted benzotriazoles, additionally acrylates that are phenyl-substituted in position 3 (cinnamic acid derivatives), optionally with cyano groups in position 2, salicylates, organic Ni complexes, as well as natural substances such as umbelliferone and the endogenous urocanic acid. In a preferred embodiment, the UV absorbers absorb UV-A and UV-B radiation as well as possible UV-C radiation and re-emit light with blue wavelengths, such that they additionally have an optical brightening effect. Preferred UV absorbers encompass triazine derivatives, e.g., hydroxyaryl-1,3,5-triazine, sulfonated 1,3,5-triazine, o-hydroxyphenylbenzotriazole and 2-aryl-2H-benzotriazole as well as bis(anilinotriazinyl-amino)stilbene disulfonic acid and their derivatives. Ultra violet absorbing pigments like titanium dioxide can also be used as UV absorbers.

O. Thickeners

The compositions can also comprise common thickeners and anti-deposition compositions as well as viscosity regulators such as polyacrylates, polycarboxylic acids, polysaccharides and their derivatives, polyurethanes, polyvinyl pyrrolidones, castor oil derivatives, polyamine derivatives such as quaternized and/or ethoxylated hexamethylenediamines as well as any mixtures thereof. Preferred compositions have a viscosity below 10,000 mPa*s, measured with a Brookfield viscosimeter at a temperature of 20° C. and a shear rate of 50 $min^{-1}$.

P. Perfumes and Colorants

The compositions can comprise further typical detergent and cleansing composition ingredients such as perfumes and/or colorants, wherein such colorants are preferred that leave no or negligible coloration on the fabrics being washed. Preferred amounts of the totality of the added colorants are below 1 wt. %, preferably below 0.1 wt. %, based on the composition. The compositions can also comprise white pigments such as e.g., $TiO_2$.

Preparations and Formulations

Preferred composition preparations and formulations according to the present inventions are selected from the group of products for treatment, protecting, care and cleansing of the skin, mouth and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced) and preferably rinse-off products, such as shampoos, shower gels, hair tonics, face cleansers, mouthwashes.

The formulations according to the invention are preferably water-based formulations. Such formulations or preparations may comprise water in a quantity of up to 99% b.w., preferably 50 to 99% b.w., based on the total weight of the preparation.

Particular preferred preparations and formulations are mouthwashes, after shaves, face cleaners, shampoos, shower gels, alcoholic and non-alcoholic deo sprays, household cleaners, liquid detergents.

In a preferred embodiment a mouth rinse preparation and formulation may preferably comprises
i) from 0 to 26.00% b.w. ethylalcohol,
ii) from 0.2 to 3.00% b.w. Cremophor CO 40 (PEG 40 hydrogenated castor oil),
iii) from 0.1 to 0.50% b.w. flavor,
iv) from 2.00 to 7% % b.w. sorbitol 70%,
v) from 0.05 to 0.5 b.w. sodiumsaccharin 450,
vi) from 0.05 to 0.5 b.w. sodiumfluoride,
vii) from 0.01 to 1.0 b.w. benzoic acid,
viii) from 0.05 to 1.0 b.w. hydroxyacetophenone according to the invention,
ix) water(deionized),
on condition that the amounts add—optionally together with additional ingredients—to 100% b.w.

In a preferred embodiment a shampoo preparation and formulation may preferably comprises
i) from 5.00-25.00% b.w. sodium lauryl ether sulfate (e.g. Texapon NSO),
ii) from 1.00-5.00% b.w. cocamidopropyl betaine (e.g. Dehyton K),
iii) from 0.10-5.00% b.w. plant oil (e.g. Avocado oil),
iv) from 0.10-10.00% b.w. fatty acid ester (e.g. Dragoxat 89: Ethy hexyl isononanoate),
v) from 1.0-3.0% b.w. sodium chloride,
vi) from 0.5-2.0% b.w. citric acid,
vii) from 0.001-2.0% b.w. perfume oil,
viii) from 0.50% b.w. phenoxyethanol. methyl-. ethyl-. butyl- and propylparaben,
ix) from 0.05-3.00% b.w. hydroxyacetophenone according to the invention,
x) water(deionized),
on condition that the amounts add—optionally together with additional ingredients—to 100% b.w.

The formulations according to the invention may also be in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular C6-C32 fatty acid C2-C30 esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or postfoaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

Methods for Stabilization of the Formulation and Fighting Body Odor

The acetophenone derivatives of formula (I) and the respective compositions according to the invention display their synergistically properties, especially as solubilizing and dissolving agent/system for flavours and fragrances and also especially for lipophilic components in formulations and compositions which especially base on water or water-alcohol.

Thus another object of the present invention is the method of improving and/or enhancing
(i) the stability and/or solubility of flavours and/or fragrances, and/or
(ii) the stability and/or solubility of lipophilic components and/or
(iii) the long lasting impression of flavours
in a cosmetic or household composition, by adding of
(a-1) a working amount of at least one acetophenone derivative of formula (I)

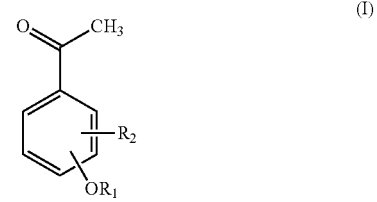

in which
$R_1$ denotes hydrogen or methyl, and
$R_2$ denotes hydrogen, hydroxyl or a —OCH3 group, or
a cosmetically or pharmaceutically acceptable salt thereof,
or by adding of
(b-1) a working amount of a flavour or fragrance composition comprising
(a) at least one acetophenone derivative of formula (I)

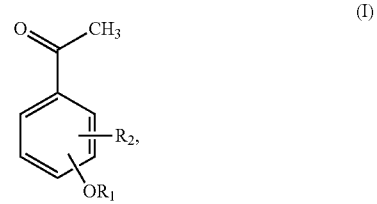

in which
$R_1$ denotes hydrogen or methyl, and
$R_2$ denotes hydrogen, hydroxyl or a —OCH3 group,
or a cosmetically or pharmaceutically acceptable salt thereof, and
(b) at least one flavor and/or fragrance and/or
(c) at least one lipophilic component, which preferably further comprises
d) water, e) at least one emulsifier or surfactant and/or
f) at least one alcohol,
to the said cosmetic or household composition.

The preferred
(i) the at least acetophenone derivatives of formula (I) are selected from the group consisting of: 2-hydroxyacetophenone, 3-hydroxyacetophenone, 4-hydroxyacetophenone,
(ii) the at least flavouring agent is selected from plant oils, synthetic or natural fragrances such as fragrances on the basis of aldehydes, ketones, alcohols, ethers, esters, hydrocarbons and mixtures thereof.

Another object of the present invention therefore covers a method for treating unpleasant body odour, in particular underarm and foot odour by topical administration a working amount of at least one acetophenone derivative of formula (I) or a (flavour) composition comprising the acetophenone derivatives of formula (I). In particular, the invention refers to the use of at least one acetophenone derivative of formula (I) or a (flavour) composition comprising the acetophenone derivatives of formula (I) as a deodorant.

It is understood that the explanations and preferred embodiments outlined above with respect to the acetophenone derivatives of formula (I) and their mixtures mutatis-mutandis apply also for the methods and uses as claimed, thus no additional repetition is necessary.

INDUSTRIAL APPLICATION

The acetophenone derivatives of formula (I) of the present invention are especially useful in cosmetic and pharmaceutical formulations and compositions, and in household products and compositions, such as detergents and cleaners.

Therefore, an important object of the invention is a cosmetic or pharmaceutical composition or a household composition, comprising the above described flavour or fragrance composition according to the invention.

A cosmetic composition according to the present invention preferably comprises
(a) from 0.05 to 5% b.w. acetophenone derivatives of formula (I);
(b) from 0.05 to 5% b.w. flavours or fragrances,
(c) from 0.05 to 10% b.w. lipophilic components,
(d) from 50 to 99% b.w. water,
(e) from 0.5 to 25% b.w. emulsifiers or surfactants,
(f) from 5 to 50% b.w. alcohols,
and optionally
(g) from 50 to 99.9% b.w. oil bodies and/or waxes;
(h) 0 to about 25% b.w. active principles;
on condition that the amounts add—optionally together with additional ingredients—to 100% b.w.

In a preferred embodiment the compositions according to the present invention comprise the components in the following amounts:
(a) from 0.05% b.w. to 5% b.w., preferably from 0.1% b.w. to 2% b.w. and more preferably from 0.3% b.w. to 1% b.w. acetophenone derivatives of formula (I);
(b) from 0.05 to 5% b.w., preferably from 0.1% b.w. to 4% b.w. and more preferably from 0.2% b.w. to 2% b.w. flavours and/or fragrances;
(c) from 0.05 to 10% b.w., preferably from 0.1% b.w. to 5% b.w. and more preferably from 0.2% b.w. to 3% b.w. lipophilic components;
(d) from 0.5 to 25% b.w., preferably from 1% b.w. to 20% b.w. and more preferably from 4% b.w. to 10% b.w. surfactants and/or emulsifiers;
(e) from 5 to 50% b.w., preferably from 10% b.w. to 30% b.w. and more preferably from 15% b.w. to 25% b.w. alcohol,
on condition that the amounts add—optionally together with water and additional ingredients—to 100% b.w.

The inventive compositions are preferably water-based, up to 99% b.w., preferably up to 95% b.w. water, based on the total amount of the end product.

The compositions according to the invention may also be o/w or w/o or multiple o/w/o or w/o/w emulsions. They can be used as an intermediate or a final product for example in the form of a lotion, a cream or a stick.

Another object of the present invention relates to the process to produce a cosmetic or household composition, comprising the steps of
(i) providing at least a flavor composition according to the invention,
(ii) providing a cosmetic or household base formulation, and
(iii) mixing the composition from step (i) with the formulation of step (ii) together.

EXAMPLES

Example 1: Water-Ethanolic Deodorant-Spray

TABLE 1

Nephelometric Turbidity Units of deodorant-spray formulation containing 4-hydroxyacetophenone

| | [% b.w.] | | | | | |
|---|---|---|---|---|---|---|
| | A | A1 | A2 | A3 | A4 | A5 |
| Ethanol | 35 | 35.0 | 35.0 | 35.0 | 35.0 | 35.0 |
| Water | 65 | 64.8 | 64.3 | 63.8 | 63.3 | 62.8 |
| Perfume oil (PN 836720) | 0 | 0.2 | 0.2 | 0.2 | 0.2 | 0.2 |
| 4-Hydroxyacetophenone | 0 | 0.0 | 0.5 | 1.0 | 1.5 | 2.0 |
| Nephelometric Turbidity Units (NTU) | | | | | | |
| Mean (n = 3) | 0.3 | 529.7 | 403.3 | 202.0 | 111.7 | 86.6 |
| Standard deviation (n = 3) | 0.1 | 2.5 | 1.2 | 1.0 | 0.6 | 0.4 |

Solubilization of perfume oil in deodorant-spray formulation can be improved by addition of 4-hydroxyacetophenone, as revealed by significantly decreasing Nephelometric Turbidity Units, when increasing amounts of 4-hydroxyacetophenone are added (Table 1). Similar results are obtained with perfume oils 962256, 906959, 906958, 906957, 906962 and 906961 (Tables 8-14).

Example 2: Ethanolic Mouthwash Concentrate

TABLE 2

Nephelometric Turbidity Units of mouthwash concentrate formulation containing 4-hydroxyacetophenone

| | [% b.w.] | | | |
|---|---|---|---|---|
| | B | B1 | B2 | B3 |
| Ethanol | 42.0 | 42.0 | 42.0 | 42.0 |
| Water | 52.5 | 52.0 | 51.5 | 51.0 |
| Mint flavour (Optamint FLO11158AA) | 4.0 | 4.0 | 4.0 | 4.0 |

TABLE 2-continued

Nephelometric Turbidity Units of mouthwash concentrate
formulation containing 4-hydroxyacetophenone

| | [% b.w.] | | | |
|---|---|---|---|---|
| | B | B1 | B2 | B3 |
| Cremophor CO40 (PEG-40 Hydrogenated Castor Oil) | 1.5 | 1.5 | 1.5 | 1.5 |
| 4-Hydroxyacetophenone | 0.0 | 0.5 | 1.0 | 1.5 |
| Nephelometric Turbidity Units (NTU) | | | | |
| Mean (n = 3) | 1100.0 | 963.3 | 238.0 | 12.4 |
| Standard deviation (n = 3) | 0.0 | 21.6 | 3.5 | 1.0 |

Solubilization of mint flavour oil in mouthwash concentrate formulation can be improved by addition of 4-hydroxyacetophenone, as revealed by significantly decreasing Nephelometric Turbidity Units, when increasing amounts of 4-hydroxyacetophenone are added (Table 2).

TABLE 3

Composition of Mint flavour (Optamint FLO11158AA)

| Ingredient | Amount |
|---|---|
| Spearmint oil *Mentha spicata* | 2 |
| Carvone L | 2 |
| Menthylacetate L | 3 |
| Eucalyptol | 5 |
| Menthone L/Isomenthone D | 9 |
| Anethole from star anise | 9 |
| Peppermint oil *Mentha piperita* | 10 |
| Menthol racemic | 10 |
| Peppermint oil *Mentha arvensis* | 20 |
| Menthol L | 30 |
| Total | 100 |

Example 3: Shampoo

TABLE 4

Nephelometric Turbidity Units of shampoo
formulation containing 4-hydroxyacetophenone

| | [% b.w.] | | | |
|---|---|---|---|---|
| | C | C1 | C2 | C3 |
| Water | 84.5 | 84 | 83.5 | 83 |
| Genapol LRO liquid (28% active content) Sodium Laureth Sulfate | 15 | 15 | 15 | 15 |
| Neutral oil Caprylic/Capric/Triglycerides | 0.5 | 0.5 | 0.5 | 0.5 |
| 4-Hydroxyacetophenone | 0.0 | 0.5 | 1.0 | 1.5 |
| Nephelometric Turbidity Units (NTU) | | | | |
| Mean (n = 3) | 1100 | 796.0 | 126.0 | 6.3 |
| Standard deviation (n = 3) | 0.0 | 1.2 | 2.2 | 0.1 |

Solubilization of neutral oil in shampoo formulation can be improved by addition of 4-hydroxyacetophenone, as revealed by significantly decreasing Nephelometric Turbidity Units, when increasing amounts of 4-hydroxyacetophenone are added (Table 4).

Example 4: Shampoo

TABLE 5

Nephelometric Turbidity Units of shampoo
formulation containing 4-hydroxyacetophenone

| | [% b.w.] | | |
|---|---|---|---|
| | D | D1 | D2 |
| Water | 88.5 | 88.0 | 87.5 |
| Genapol LRO liquid (28% active content) Sodium Laureth Sulfate | 12.0 | 12.0 | 12.0 |
| Perfume oil (PN 962256) | 1.7 | 1.7 | 1.7 |
| 4-Hydroxyacetophenone | 0.0 | 0.5 | 1.0 |
| Nephelometric Turbidity Units (NTU) | | | |
| Mean (n = 3) | 208.0 | 3.5 | 1.2 |
| Standard deviation (n = 3) | 1.0 | 0.3 | 0.0 |

Solubilization of perfume oil in shampoo formulation can be improved by addition of 4-hydroxyacetophenone, as revealed by significantly lower Nephelometric Turbidity Units (Table 5).

Example 5: Odour Intensity Increase of Dihydromyrcenol by 4-hydroxyacetophenone

Ten microliters of the solutions were applied on a blotter and stored at room temperature. The blotters were evaluated by 13 panellists with a2-AFC-Test (ISO 5495, paired comparison). Panellists marked the more intense sample and then the intensity was assigned for both samples on a scale of 1 to 9 (1: odourless, 9: very strong). Mean and standard deviation of intensity scores were calculated from one assessment of the 13 panellists.

TABLE 6

Odour intensity increase of
Dihydromyrcenol by 4-hydroxyacetophenone

| | Composition (%) | | | |
|---|---|---|---|---|
| | E | E1 | F | F1 |
| Ethanol | 81.0 | 76.5 | 81.0 | 76.5 |
| Water | 9.0 | 8.5 | 9.0 | 8.5 |
| Dihydromyrcenol | 10.0 | 10.0 | 10.0 | 10.0 |
| 4-Hydroxyacetophenone | 0 | 5.0 | 0 | 5.0 |
| Intensity scores | Fresh | | Stored (1 h) | |
| Mean (n = 13) | 3.54 | 3.85 | 1.69 | 3.15 |
| Standard deviation (n = 13) | 0.66 | 1.07 | 0.63 | 0.69 |

Results: Dihydromyrcenol showed a higher odour intensity after 1 h as compared to a reference, when combined with 4-hydroxyacetophenone (Table 6).

Example 6: Reduction of Bathroom Malodour by 4-Hydroxyacetophenone

Fifteen Expert panellists evaluated the samples from 500 ml wide necked glass jars. One microliter of the sample (dissolved in 9 microliters of diethylphatlate) and one microliter bathroom malodour (1% solution in Triethyl citrate) were injected on different places of a filter paper. The filter paper was placed in the glass jar and left closed for >16 hours for equilibration. Malodour intensities were evaluated on scales of 1 (odourless) to 9 (very strong) with 6 being the reference of the malodour sample. Mean and standard deviation of intensity scores were calculated from three independent experiments.

TABLE 7

Reduction of bathroom malodour by 4-hydroxyacetophenone

| | Amount applied on filter paper (µl) | | |
|---|---|---|---|
| | G | G1 | G2 |
| Bathroom malodour standard | 1.0 | 0 | 1.0 |
| 4-hydroxyacetophenone | 0 | 1.0 | 1.0 |
| Intensity scores | | | |
| Mean (n = 15) | 6.00 | 2.31 | 2.50 |
| Standard deviation (n = 15) | — | 1.31 | 1.55 |
| Reduction versus malodour standard | | | 3.50 |

Results: Bathroom malodour standard combined with 4-hydroxyacetophenone revealed an intensity score of 2.50, as opposed to 6.00 of the unamended bathroom maladour standard. This demonstrates the strong reduction (3.50 scores) of bathroom malodour by 4-hydroxyacetophenone (Table 7).

Examples 7: Perfume Oil Compositions

The perfume oil compositions of the following tables 8-14 are to be combined with acetophenone derivatives of formula (I) of the present invention.

TABLE 8

Composition of perfume oil 836720

| Ingredient | Amount |
|---|---|
| ALDEHYDE C14 SO-CALLED | 2 |
| ALLYL AMYL GLYCOLATE 10% DPG | 5 |
| ANISIC ALDEHYDE PURE | 5 |
| APPLE OLIFFAC TYPE | 10 |
| Benzylacetat | 50 |
| BERGAMOT IDENTOIL ® COLOURLESS | 15 |
| BHT IONOL | 3 |
| CANTHOXAL | 5 |
| CETALOX 10% IPM | 3 |
| CITRONELLOL 950 | 40 |
| DAMASCENONE TOTAL 1% DPG | 5 |
| DAMASCONE ALPHA 10% DPG | 5 |
| DAMASCONE DELTA 10% DPG | 2 |
| DIMETHYL BENZYL CARBINYL BUTYRATE | 2 |
| DIPROPYLENE GLYCOL | 175 |
| EBANOL | 2 |
| ETHYL DECADIENOATE TRANS CIS-2,4 10% IPM | 2 |
| FLOROSA | 5 |
| FRAMBINON ® 10% DPG | 7 |
| GALAXOLIDE 50% IN IPM | 100 |
| GALBEX TYPE BASE | 1 |
| GERANYL ACETATE PURE | 2 |
| HEDIONE | 30 |
| HELIOTROPIN | 10 |
| HEXENYL ACETATE CIS-3 10% DPG | 1 |
| HEXENYL SALICYLATE CIS-3 | 5 |
| HEXYL CINNAMIC ALDEHYDE ALPHA | 70 |
| HEXYL SALICYLATE | 50 |
| HYDROXY CITRONELLAL | 10 |
| ISO E SUPER | 15 |
| ISORALDEINE 70 | 20 |
| LEAFOVERT ® | 1 |
| LILIAL | 60 |
| LINALOOL | 60 |
| LINALYL ACETATE | 20 |
| LYRAL | 7 |
| MANZANATE | 2 |

TABLE 8-continued

Composition of perfume oil 836720

| Ingredient | Amount |
|---|---|
| PHENOXANOL | 7 |
| PHENYLETHYL ALCOHOL | 120 |
| SANDAL MYSORE CORE | 2 |
| SANDRANOL ® | 7 |
| STYRALYL ACETATE | 3 |
| TAGETES RCO 10% TEC | 2 |
| TERPINEOL PURE | 20 |
| TETRAHYDROGERANIOL 10% DPG | 5 |
| TONALIDE | 7 |
| VERTOCITRAL 10% DPG | 5 |
| VERTOFIX | 15 |
| Total | 1000 |

TABLE 9

Composition of perfume oil 962256

| Ingredient | Amount |
|---|---|
| AMBERWOOD ® F | 20 |
| ANISALDEHYD REIN | 10 |
| BENZYLACETAT | 2 |
| BERGAMOTT ECO ESSENCE | 2 |
| CEDRAMBER | 5 |
| CUMARIN | 5 |
| CYCLAMENALDEHYD | 7 |
| DIHYDROMYRCENOL | 20 |
| DIPROPYLENGLYCOL | 464 |
| ETHYLLINALOOL | 5 |
| ETHYLMALTOL | 1 |
| ETHYLVANILLIN | 50 |
| GALAXOLID 50% IN DPG | 125 |
| HYDROXYCITRONELLAL | 1 |
| ISOEUGENOL 10% DPG | 5 |
| ISOEUGENOLACETAT | 1 |
| LINALYLACETAT | 10 |
| LYRAL | 3 |
| MUSCENONE 10% DPG | 2 |
| PATCHOULIOEL ENTF. | 2 |
| POLYSANTOL 10% DPG | 2 |
| SANDRANOL ® | 3 |
| TETRAHYDROLINALOOL | 20 |
| TONALID | 75 |
| YSAMBER ® K | 60 |
| Total | 900 |

TABLE 10

Composition of perfume oil 906959

| Ingredient | Amount |
|---|---|
| ALDEHYDE C 8 10% DPG | 5 |
| ALDEHYDE C10 | 1 |
| ALDEHYDE C14 SO-CALLED | 0.5 |
| AMAROCIT ® | 4 |
| AMBROX DL 10% DPG | 2 |
| ANISIC ALDEHYDE PURE | 4 |
| BOURGEONAL | 3 |
| CARVONE L 10% DPG | 3 |
| DAMASCONE ALPHA 1% IPM | 8 |
| DECALACTONE GAMMA | 0.5 |
| DIHYDRO MYRCENOL | 30 |
| DIHYDRO MYRCENYL ACETATE | 37 |
| DIMETHYL BENZYL CARBINYL ACETATE | 1.5 |
| DIPROPYLENE GLYCOL | 351.3 |
| DYNASCONE MELANGE 1:1 10% DPG | 0.5 |
| FLORAZON 10% DPG | 6 |
| FLOROSA | 70 |

TABLE 10-continued

Composition of perfume oil 906959

| Ingredient | Amount |
| --- | --- |
| FRAMBINON ® 1% DPG | 2 |
| FREESIOL/CORPS 119 | 5 |
| GIVESCONE | 0.7 |
| HEDIONE | 40 |
| HEXENYL SALICYLATE CIS-3 | 2 |
| HEXYL SALICYLATE | 40 |
| IONONE ALPHA | 50 |
| IONONE BETA | 4.5 |
| ISO E SUPER | 10 |
| ISOBUTYL CINNAMATE | 1 |
| ISOMUSCONE ® 50% IPM | 1 |
| ISOPROPYL MYRISTATE | 170 |
| LEAFOVERT ® 10% DPG | 3 |
| MACROLIDE ® SUPRA 50% TEC | 100 |
| MAJANTOL ® | 50 |
| MANDARIN ALDEHYDE 10% IN TEC | 1 |
| MEFRANAL | 1 |
| METHYL ANTHRANILATE 1% DPG | 2 |
| METHYL NAPHTYL KETONE BETA CRYST 10% IPM | 1 |
| NEROLIDOL | 15 |
| PHENOXANOL | 40 |
| PHENYLETHYL ACETATE | 0.5 |
| PHENYLETHYL ALCOHOL BA FREE | 50 |
| PHENYLETHYL DIMETHYL CARBINOL | 30 |
| PHENYLETHYL PHENYLACETATE | 2 |
| PHENYLETHYL SALICYLATE | 1 |
| ROSAPHEN ® | 20 |
| ROSE OXIDE HIGH CIS 10% DPG | 1 |
| SANDRANOL ® | 1.5 |
| TERPINEOL RECT. | 6 |
| TETRAHYDRO CITRAL | 0.5 |
| TETRAHYDRO LINALOOL | 20 |
| VELOUTONE 10% DPG | 1 |
| Total | 1200 |

TABLE 11

Composition of perfume oil 906958

| Ingredient | Amount |
| --- | --- |
| ALDEHYDE C12 MNA 10% DPG | 1 |
| ALLYL AMYL GLYCOLATE | 3 |
| AMBROXIDE | 0.5 |
| AMYL SALICYLATE N | 15.5 |
| BENZYL ACETATE | 1.5 |
| BENZYL BENZOATE M | 119.7 |
| BENZYL SALICYLATE | 23 |
| BERGAMOT SYNTHESSENCE AFRIC. | 38.5 |
| CALONE 10% DPG | 3 |
| CASHMERAN | 1 |
| CASSIS 345B TYPE BASE | 0.8 |
| CASTOREUM GIVCO 116/3 | 1 |
| CEDAR LEAF OIL | 1 |
| CEDRAMBER | 15.5 |
| CISTUS LABDANUM ABS. SIS 30% TEC | 3.7 |
| CITRAL FF | 1 |
| CLOVE BUD OIL | 1.5 |
| CYCLAMEN ALDEHYDE | 3 |
| DAMASCONE DELTA | 0.5 |
| DECENAL CIS-4 1% DPG | 3 |
| DIHYDRO MYRCENOL | 84.5 |
| DIPROPYLENE GLYCOL | 166.7 |
| ESTRAGOLE NAT. | 1.1 |
| EVERNYL | 6 |
| FIR NEEDLE SIBERIA H | 3 |
| FLORAZON 10% DPG | 3 |
| FLOROSA | 3 |
| GALAXOLIDE 50% IN BB | 131 |
| GALBANUM OIL 1% DPG | 4 |
| GALBEX REPLACEMENT | 7.5 |

TABLE 11-continued

Composition of perfume oil 906958

| Ingredient | Amount |
| --- | --- |
| GERANIUM IDENTOIL AFRIKA | 1 |
| HEDIONE | 61.5 |
| HELIONAL | 15.5 |
| HELIOTROPIN | 1 |
| HEXALACTONE GAMMA 10% DPG | 5.5 |
| HEXENOL CIS-3 | 0.5 |
| HEXENYL ACETATE CIS-3 10% DPG | 1.5 |
| HYDROXY CITRONELLAL | 4 |
| ISO E SUPER | 38.5 |
| ISOBORNYL CYCLOHEXANOL | 16.5 |
| ISOBUTYL QUINOLINE 10% DPG | 1.5 |
| LAVANDINOIL ABRIALIS NAT. | 5.5 |
| LIGUSTRAL | 0.5 |
| LILIAL | 4.5 |
| LINALOOL | 7.5 |
| LINALYL ACETATE | 7.5 |
| MANZANATE 10% DPG | 1 |
| METHYL IONONE GAMMA PURE/IFF | 3 |
| ORANGE OIL BRASIL | 11.5 |
| ORIGANUM OIL | 0.5 |
| PATCHOULI OIL DECOL. | 2 |
| PINOACET ALDEHYDE | 0.5 |
| PRECYCLEMONE B | 1.5 |
| SANDALORE | 7.5 |
| SANDALWOOD OIL EAST IND. | 0.5 |
| SANDRANOL ® | 7.5 |
| STAR ANISE OIL CRUDE 10% DPG | 2 |
| STEMONE 10% DPG | 1 |
| TANGERINE CRAVO OIL BRAZIL | 1.5 |
| TONALIDE | 4.5 |
| UNDECAVERTOL 1% DPG | 2 |
| VANILLIN 10% DPG | 0.5 |
| VERTOFIX | 133 |
| Total | 1000 |

Example 12: Composition of Perfume Oil 906957

| Ingredient | Amount |
| --- | --- |
| ALDEHYDE C10 | 0.5 |
| ALLYL AMYL GLYCOLATE | 1 |
| AMBRETTOLIDE | 4.8 |
| AMBRINOL S | 0.6 |
| AMBROXIDE | 8 |
| BENZYL ACETATE | 4.2 |
| BENZYL SALICYLATE | 13 |
| BERGAMOT OIL | 35 |
| BHT IONOL | 3.5 |
| CITRAL FF | 0.8 |
| CITRONELLOL 950 | 7 |
| CITRONELLYL ACETATE EXTRA | 0.9 |
| COUMARIN | 0.7 |
| CYPRESS OIL | 1 |
| DECALACTONE GAMMA | 2.5 |
| DIHYDRO IONONE BETA | 0.5 |
| DIHYDRO MYRCENOL | 2.3 |
| DIMETHYL BENZYL CARBINYL BUTYRATE | 1 |
| DIPROPYLENE GLYCOL | 51.3 |
| ETHYL LINALOOL | 48 |
| ETHYL VANILLIN | 3.5 |
| ETHYLENE BRASSYLATE | 32 |
| EVERNYL | 1.2 |
| EXALTENONE 942008 | 2.5 |
| FLOROSA | 27 |
| FRAMBINON ® | 0.5 |
| GERANIOL SUPER | 0.5 |
| GERANYL ACETATE PURE | 0.5 |
| GLOBALIDE ® | 87 |
| HEDIONE HC/70 | 110 |
| HELIONAL | 20 |

-continued

| Ingredient | Amount |
| --- | --- |
| HELIOTROPIN | 25 |
| HEXENOL CIS-3 | 0.5 |
| HEXENYL BENZOATE CIS-3 | 2.5 |
| HEXENYL ISOBUTYRATE CIS-3 | 4.8 |
| HEXYL CINNAMIC ALDEHYDE ALPHA | 8 |
| HYDROXY CITRONELLAL | 6.5 |
| INDOLE FF | 0.7 |
| ISO E SUPER | 198 |
| ISORALDEINE 95 | 36 |
| JASMIN LACTONE | 1 |
| LEAFOVERT ® | 0.5 |
| LINALOOL | 36 |
| LINALYL ACETATE | 16 |
| MACROLIDE ® SUPRA | 35 |
| MANDARIN OIL ITAL. | 25 |
| METHYL ANTHRANILATE | 0.5 |
| METHYL NAPHTYL KETONE BETA CRYST | 12 |
| MUSCENONE | 6 |
| NEROL 900 | 0.5 |
| Neo Heliopan ® OS | 4 |
| ORANGE OIL BRASIL | 18 |
| PHENYLETHYL ALCOHOL | 6.5 |
| POLYSANTOL | 11.5 |
| SANDRANOL ® | 68 |
| STYRALYL ACETATE | 0.7 |
| VANILLIN | 5 |
| VERTOCITRAL | 0.5 |
| Total | 1000 |

TABLE 13

| Composition of perfume oil 906962 | |
| --- | --- |
| Ingredient | Amount |
| AGRUMEX LC | 43.9 |
| ALCOHOL C 6 | 0.6 |
| ALDEHYDE C 7 10% DPG | 0.6 |
| ALDEHYDE C14 SO-CALLED 10% DPG | 3.9 |
| ALLYL CYCLOHEXYL PROPIONATE | 1.9 |
| AMBROXIDE 10% IPM | 2.6 |
| AMYL SALICYLATE | 3.2 |
| APHERMATE | 0.6 |
| APPLE GREEN AROMABASE W/O BHA | 12.9 |
| AURANTIOL 50% DPG | 1.3 |
| BENZALDEHYDE DD 10% DPG | 1.3 |
| BENZYL ACETATE | 1.3 |
| BORNEOL L/ISOBORNEOL 65/35 | 1.3 |
| CASSIS 345B TYPE BASE | 0.6 |
| CHAMOMILE OIL BLUE 10% DPG | 2.6 |
| COUMARIN 10% DPG | 1.9 |
| DECALACTONE GAMMA | 0.6 |
| DIHYDRO MYRCENOL | 29 |
| DIMETHYL BENZYL CARBINYL ACETATE | 1.3 |
| DIPROPYLENE GLYCOL | 603.3 |
| DYNASCONE MELANGE 1:1 10% DPG | 2.6 |
| ETHYL CAPROATE | 4.5 |
| ETHYL PROPIONATE 10% DPG | 0.6 |
| EUCALYPTUS OIL GLOBULUS 80/85% | 4.5 |
| EXALTENONE 942008 10% DPG | 1.3 |
| FRAMBINON ® | 0.6 |
| GERANYL NITRILE REPLACEMENT | 3.2 |
| HERBAFLORAT | 9.7 |
| HERBYL PROPIONATE | 24.5 |
| HEXENOL CIS-3 10% DPG | 5.2 |
| HEXENYL ACETATE CIS-3 10% DPG | 1.9 |
| HEXYL ACETATE | 9.7 |
| HEXYL BUTYRATE 10% DPG | 11.6 |
| HEXYL CINNAMIC ALDEHYDE ALPHA | 1.3 |
| HEXYL ISOBUTYRATE 10% DPG | 1.9 |
| HEXYL SALICYLATE | 9.7 |
| HYACINTH BODY | 4.5 |
| IONONE BETA | 3.9 |
| ISO E SUPER | 9.7 |

TABLE 13-continued

| Composition of perfume oil 906962 | |
| --- | --- |
| Ingredient | Amount |
| ISOBORNYL ACETATE | 18.1 |
| ISOBORNYL PROPIONATE | 2.6 |
| ISOBUTYL QUINOLINE 1% DPG | 1.9 |
| ISOPENTYRATE | 0.6 |
| ISORALDEINE 70 | 25.8 |
| LAVANDINOIL ABRIALIS NAT. | 1.3 |
| LINALOOL | 7.7 |
| LINALOOL OXIDE | 0.6 |
| LINALYL ACETATE | 3.2 |
| LITSEA CUBEBA OIL DIST. 10% DPG | 1.3 |
| MAYOL | 2.6 |
| MENTHANYL ACETATE | 1 |
| METHYL ACETOPHENONE PARA 10% DPG | 1.3 |
| METHYL NAPHTYL KETONE BETA CRYST | 1.3 |
| NEROLIN BROMELIA | 0.6 |
| NEROLIN YARA YARA CRIST. | 1.3 |
| OCTENYL ACETATE-1,3 10% DPG | 1.3 |
| ORANGE OIL BRASIL | 32.3 |
| ORYCLON SPECIAL | 32.3 |
| PATCHOULI OIL DECOL. MD 10% DPG | 1.3 |
| PHENYLETHYL ACETATE 10% DPG | 1.9 |
| PHENYLETHYL ALCOHOL | 3.9 |
| RHUBAFURANE 10% DPG | 1.3 |
| ROSE DE MAI-BASE | 0.6 |
| STEMONE 10% DPG | 0.6 |
| TERPINYL ACETATE | 16.1 |
| UNDECAVERTOL | 2.6 |
| VANILLIN EXTRA (EX CATECHOL) 10% DPG | 1.9 |
| VERTOFIX | 6.5 |
| YLANG OIL TYPE BASE | 0.6 |
| Total | 1000 |

TABLE 14

| Composition of perfume oil 906961 | |
| --- | --- |
| Ingredient | Amount |
| ALLYL AMYL GLYCOLATE | 5 |
| AMBRINOL S 10% DPG | 2 |
| AMBROXIDE 10% IPM | 2 |
| BENZYL BENZOATE M | 4.2 |
| BERGAMOT IDENTOIL ® COLOURLESS | 100 |
| BHT IONOL | 3 |
| BORONAL 10% DPG | 1 |
| CALONE 0.1% DPG | 0.5 |
| CARYOPHYLLENE ACETATE | 17.6 |
| CEDARWOOD OIL 10% DPG | 2 |
| CEDRYL ACETATE | 2.1 |
| CITRAL FF | 10 |
| CITRONELLOL 950 | 10 |
| CYCLOGALBANAT ® | 10 |
| DAMASCONE ALPHA | 2 |
| DECALACTONE DELTA 1% DEP | 0.5 |
| DIHYDRO MYRCENOL | 200 |
| DIPROPYLENE GLYCOL | 498.7 |
| EVERNYL | 2.1 |
| FIR BALSAM ABS. 10% DPG | 1 |
| GALAXOLIDE 50% IN DEP | 10 |
| GALBANUM ARTESSENCE | 3 |
| GERANIUM IDENTOIL AFRIKA | 5 |
| GERANYL NITRILE REPLACEMENT | 3 |
| HEDIONE UNSTAB. | 10 |
| HERCOLYN D-E | 34.2 |
| HEXYL ACETATE | 1 |
| HEXYL CINNAMIC ALDEHYDE ALPHA | 44 |
| HYDROXY CITRONELLAL | 25 |
| ISOBORNYL CYCLOHEXANOL | 4.2 |
| ISOMUSCONE ® | 0.6 |
| ISORALDEINE 70 | 10.1 |
| KETAMBER 10% IN TEC | 2 |
| LAVANDIN GROSSO BM | 30 |

TABLE 14-continued

Composition of perfume oil 906961

| Ingredient | Amount |
|---|---|
| MACROLIDE ® SUPRA 50% TEC | 0.6 |
| MALTOL 1% DPG | 10 |
| METHYL NAPHTYL KETONE BETA CRYST | 5 |
| MOUSSE C ABS. F0420 REPLACEMENT | 1 |
| MUSCENONE | 0.5 |
| ORYCLON SPECIAL | 32.5 |
| ORYCLON@ HC | 17.5 |
| PALISANDAL | 35 |
| PEPPERMINT ARV. OIL DMO | 5 |
| PETITGRAIN OIL PARAG. BOLEADOR | 10 |
| PINE NEEDLE ABS. | 0.6 |
| ROSEMARY OIL BM | 10 |
| SANDALWOOD OIL MELANGE 1 10% DPG | 2 |
| TERPINYL ACETATE | 100 |
| TONALIDE | 6 |
| VEGETABLE OIL TRIGLYCERIDE | 4.5 |
| VERTOCITRAL | 1 |
| VERTOFIX 10% DPG | 2 |
| VETIVER OIL HAITI 10% DPG | 1 |
| Total | 1300 |

The invention claimed is:

1. A formulation consisting of:
   (a) from 0.05 to 5.0% by weight of 4-hydroxyacetophenone or a cosmetically or pharmaceutically acceptable salt thereof;
   (b) from 0.05 to 5.0% by weight of at least one lipophilic flavor and/or fragrance having a different structure from said component (a);
   (c) from 0.05 to 10% by weight lipophilic components;
   (d) from 0.5 to 25% by weight of at least one emulsifier selected from the group consisting of
   products of the addition of 2 to 30 mol ethylene oxide and/or 0 to 5 mol propylene oxide onto linear $C_8$-$C_{22}$ fatty alcohols, onto $C_{12}$-$C_{22}$ fatty acids and onto alkyl phenols containing 8 to 15 carbon atoms in the alkyl group;
   $C_{12}$-$C_{18}$ fatty acid monoesters and diesters of addition products of 1 to 30 mol ethylene oxide onto glycerol;
   glycerol mono- and diesters and sorbitan mono- and diesters of saturated and unsaturated fatty acids containing 6 to 22 carbon atoms and ethylene oxide addition products thereof;
   addition products of 15 to 60 mol ethylene oxide onto castor oil and/or hydrogenated castor oil;
   polyol esters;
   addition products of 2 to 15 mol ethylene oxide onto castor oil and/or hydrogenated castor oil;
   partial esters based on linear, branched, unsaturated or saturated $C_{6-22}$ fatty acids, ricinoleic acid, or 12-hydroxystearic acid, or glycerol, polyglycerol, pentaerythritol, dipentaerythritol, or alkyl glucosides;
   mono-, di and trialkyl phosphates and mono-, di- and/or tri-PEG-alkyl phosphates and salts thereof;
   wool wax alcohols;
   polysiloxane/polyalkyl polyether copolymers;
   mixed esters of pentaerythritol, fatty acids, citric acid and fatty alcohol and/or mixed esters of $C_{6-22}$ fatty acids, methyl glucose and polyols;
   polyalkylene glycols;
   glycerol carbonate;
   partial glycerides;
   sorbitan esters;
   aliphatic $C_{12}$-$C_{22}$ fatty acids;
   betaines;
   N-alkyl glycines;
   N-alkyl propionic acids;
   N-alkylaminobutyric acids;
   N-alkyliminodipropionic acids;
   N-hydroxyethyl-N-alkylamidopropyl glycines;
   N-alkyl taurines;
   N-alkyl sarcosines;
   2-alkylaminopropionic acids; and
   alkylaminoacetic acids containing around 8 to 18 carbon atoms in the alkyl group;
   (e) from 5% by weight to 50% by weight alcohol;
   (f) water; and
   (g) a further additive selected from the group consisting of superfatting agent, consistency factor, rheology additive, polymer, silicone, wax, stabilizer, primary sun protection factor, secondary sun protection factor, anti-ageing active, cooling agent, antimicrobial agent, dye, fragrance, flavor, aroma compounds, organic solvent, sequestrant, chelating agent, and thickener, on condition that the amounts of (a)-(g) which are present in the formulation add up to 100% by weight;
   wherein the formulation is selected from the group consisting of a cosmetic formulation, a pharmaceutical formulation, and a household formulation.

2. A clear transparent solution consisting of:
   (a) from 0.05 to 5.0% by weight of 4-hydroxyacetophenone or a cosmetically or pharmaceutically acceptable salt thereof;
   (b) from 0.05 to 5.0% by weight of at least one lipophilic flavor and/or fragrance having a different structure from said component (a);
   (c) from 0.05 to 10% by weight lipophilic components;
   (d) from 0.5 to 25% by weight of at least one emulsifier selected from the group consisting of
   products of the addition of 2 to 30 mol ethylene oxide and/or 0 to 5 mol propylene oxide onto linear $C_8$-$C_{22}$ fatty alcohols, onto $C_{12}$-$C_{22}$ fatty acids and onto alkyl phenols containing 8 to 15 carbon atoms in the alkyl group;
   $C_{12}$-$C_{18}$ fatty acid monoesters and diesters of addition products of 1 to 30 mol ethylene oxide onto glycerol;
   glycerol mono- and diesters and sorbitan mono- and diesters of saturated and unsaturated fatty acids containing 6 to 22 carbon atoms and ethylene oxide addition products thereof;
   addition products of 15 to 60 mol ethylene oxide onto castor oil and/or hydrogenated castor oil;
   polyol esters;
   addition products of 2 to 15 mol ethylene oxide onto castor oil and/or hydrogenated castor oil;
   partial esters based on linear, branched, unsaturated or saturated $C_{6-22}$ fatty acids, ricinoleic acid, or 12-hydroxystearic acid, or glycerol, polyglycerol, pentaerythritol, dipentaerythritol, or alkyl glucosides;
   mono-, di and trialkyl phosphates and mono-, di- and/or tri-PEG-alkyl phosphates and salts thereof;
   wool wax alcohols;
   polysiloxane/polyalkyl polyether copolymers;
   mixed esters of pentaerythritol, fatty acids, citric acid and fatty alcohol and/or mixed esters of $C_{6-22}$ fatty acids, methyl glucose and polyols;
   polyalkylene glycols;
   glycerol carbonate;
   partial glycerides;
   sorbitan esters;
   aliphatic $C_{12}$-$C_{22}$ fatty acids;

betaines;
N-alkyl glycines;
N-alkyl propionic acids;
N-alkylaminobutyric acids;
N-alkyliminodipropionic acids;
N-hydroxyethyl-N-alkylamidopropyl glycines;
N-alkyl taurines;
N-alkyl sarcosines;
2-alkylaminopropionic acids; and
alkylaminoacetic acids containing around 8 to 18 carbon atoms in the alkyl group;
(e) from 5% to 50% by weight alcohol;
(f) water; and
(g) a further additive selected from the group consisting of superfatting agent, consistency factor, rheology additive, polymer, silicone, wax, stabilizer, primary sun protection factor, secondary sun protection factor, anti-ageing active, cooling agent, antimicrobial agent, dye, fragrance, flavor, aroma compounds, organic solvent, sequestrant, chelating agent, and thickener, on condition that the amounts of (a)-(g) which are present in the formulation, add up to 100% by weight;
wherein the formulation is selected from the group consisting of a cosmetic formulation, a pharmaceutical formulation, and a household formulation.

* * * * *